US005968894A

United States Patent [19]
Lingwood et al.

[11] Patent Number: 5,968,894
[45] Date of Patent: Oct. 19, 1999

[54] VEROTOXIN PHARMACEUTICAL COMPOSITIONS AND MEDICAL TREATMENTS THEREWITH

[76] Inventors: Clifford A. Lingwood; Richard Hill, both of 555 University Avenue, Toronto, Canada; Hannah Farkas-Himsley, deceased, late of Jerusalem, Israel; Ruth Geva, Mishol Ha'Magaliit 17, Jerusalem, Israel, 97277; Leorah Kroyanker, 132 Hakfi Street Malha, Jerusalem 96952, Israel, both executors of said Hannah Fakar-Himsley, deceased

[21] Appl. No.: 08/563,394

[22] Filed: Nov. 28, 1995

Related U.S. Application Data

[63] Continuation-in-part of application No. 08/386,957, Feb. 10, 1995, abandoned.

[30]    Foreign Application Priority Data

Feb. 22, 1994 [CA] Canada ................................. 2116179

[51] Int. Cl.$^6$ ............................ A01N 37/18; A61K 38/00
[52] U.S. Cl. ................................................................ 514/2
[58] Field of Search ...................................................... 514/2

[56]                References Cited

PUBLICATIONS

Costello, P., et al., "Human cerebral endothelium: Isolation and characterization of cells derived from microvessels of non–neoplastic and malignant glial tissue", *J. Neuro–Oncology*, vol. 8, pp. 231–243 (1990).

Pintus, C., et al., "Endothelial Cell Growth Supplement: a Cell Cloning Factor that Promotes the Growth of Monoclonal Antibody Producing Hybridoma Cells", *Journal of Immunological Methods*, vol. 61, pp. 195–200 (1983).

Ramotar, K., et al., "Characterization of Shiga–like toxin I B subunit purified from overproducing clones of the SLT–I B cistron", *Biochem. J.*, vol. 272, pp. 805–811 (1990).

Rutka, J.T., et al., "Characterization of Normal Human Brain Cultures", *Laboratory Investigation*, vol. 55, No. 1, p. 71 (1986).

Sandvig, K., et al., "Toxin–Induced Cell Lysis: Protection by 3–Methyladenine and Cycloheximide", *Experimental Cell Research*, vol. 200, pp. 253–262 (1992).

Farkas–Himsley, et al: "Bacterial Proteinaceous Products (Bacteriocins) as Cytotoxic Agents of Neoplasia" Cancer Research 36, 3562–3567 (Oct. 1976).

Hill, et al: "Further Studies of the Action of a Partially Purified Bacteriocin against a Murine Fibrosarcoma" *Cancer Research*, 51, 1359–1365 (Mar. 1, 1991).

Karmali: "Infection by Verocytotoxin–Producing *Escherichia coli*", Clinical Microbiology Reviews, Jan., 1989 pp. 15–38, vol. 2, No. 1.

Riley, et al: "Hemorrhagic Colitis Associated witha a Rare *Escherichia Coli* Serotype", The New England Journal of Medicine, vol. 308, No. 12, 681–685 (Mar. 24, 1983).

Lingwood: "Verotoxins and Their Glycolipid Receptors", Advances in Lipid Research, vol. 25, 189–211 (1993).

Van De Kar, et al: "Tumor Necrosis Factor and Interleukin–1 Induce Expression of the Verocytotoxin Receptor Globotriaosylceramide on Human Endothelial Cells: Implications for the Pathogenesis of the Hemolytic Uremic Syndrome", Blood, vol. 80, No. 11, (Dec. 1, 1992) pp. 2755–2764.

Orbig, et al: "Endothelial Heterogeneity inShiga Toxin Receptors and Responses", The Journal of Biological Chemistry, vol. 268, No. 21, Jul. 25, 1993, pp. 15484–15488.

Lingwood: "Verotoxin–Binding in Human Renal Sections", Nephron 1994; 66; 21–28.

Cohen, et al: "Expression of Glycolipid Receptors to Shiga–like Toxin on Human B Lymphocytes: a Mechanism for the failure of long–lived antibody response to dysenteric disease", International Immunology, vol. 2, No. 1, 1990, pp. 1–8.

Gregory, et al: "Identificatioof a Subset of Normal B Cells with a Burkitt's Lymphoma (BL)–like Phenotype" The Journal of Immunology, vol. 139, No. 1, (Jul. 1, 1987) pp. 313–318.

Maloney, et al: "CD19 has a Potential CD77 (Globotriaosyl Ceramide)–binding Site with Sequence Similarity to Verotoxin B–subunits: Implications of Molecular Mimicry for B Cell Adhesion and Enterochemorrhagic *Escherichia Coli* Pathogenesis", J. Exp. Med. vol. 180 (Jul. 1994) 191–201.

Maloney, et al: "Interaction of Verotoxins with Glycosphingolipids", Trends in Glycoscience and Glycotechnology vol. 5, No. 21 (Jan. 1993) pp. 23–31.

Li, et al: "Accumlation of Globotriaosylceramide in a case of Leiomyosarcoma", Biochemistry J. (1986) vol. 240, 925–927.

Mannori, et al: "Role of Glycolipids in the Metastatic Process: Characteristics of Neutral Glycolipids in Clones with Different Metastatic Potentials Isolated from a Murine Fibrosarcome Cell Line", Int. J. Cancer vol. 45, (1990) pp. 984–988.

Ohyama, et al: "Changes in Clycolipid Expression in Human Testicular Tumor", Int. J. Cancer, vol. 45, (1990) pp. 1040–1044.

Naiki, et al: "Human Erythrocyte P and $P^k$ Blood Group Antigens: Identification as Glycosphingolipids" Biochemical and Biophysical Research Communications, vol. 60, No. 3, 1974—1105–1111.

(List continued on next page.)

*Primary Examiner*—Patricia Duffy
*Attorney, Agent, or Firm*—Lahive & Cockfield, LLP; Giulio A. DeConti, Jr.

[57]                ABSTRACT

Pharmaceutical compositions comprising known verotoxins, particularly, verotoxin 1 and their pentameric subunit B, have been found to be useful in the treatment of mammalian neoplasia, particularly, brain cancer, ovarian cancer, breast cancer and skin cancer. Although verotoxin 1 has previously been shown to have anti-neoplastic activity in vitro, non-lethal doses of verotoxin 1 have been shown to be therapeutically anti-neoplastic in vivo. Use of a sensitizer, such as sodium butyrate, enhances the efficacy of verotoxins and their subunit B.

12 Claims, 14 Drawing Sheets

OTHER PUBLICATIONS

Pallesen, et al: Distribution of the Burkitt's Lymphoma–associated Antigen (BLA) in Normal Human Tissue and Malignant Lymphoma as Defined by Immunohistological Staining with Monoclonal Antibody 38.13* J Cancer Res Clin Oncol (1987) 113: pp. 67–86.

Kasai, et al: "Tissue Distribution of the $P^k$ Antigen as Determined by a Monoclonal Antibody", Journal of Immunogenetics (1985) vol. 12, pp. 213–220.

Pudymaitis, et al: "Susceptibility to Verotoxin as a Function of the Cell Cycle", Journal of Cellular Physiology, 150: (1992) pp. 632–639.

Lingwood, "Glycolipid Modificationof α2 Interferon Binding", Biochem, J. vol. 283, (1992) pp. 25–26.

Sandvig, et al: "Retrograde Transport of Endocytossed Shiga Toxin to the Endoplasmic Reticulum", Nature vol. 358, (Aug. 6, 1992) pp. 510–512.

Head, S.C. et al., *FEMS Microbiology Letters*, 51:211–16, 1988.

Mangeney, M. et al., *Cancer Research*, 53: 5314–19, 1993.

VEROTOXIN PHARMACEUTICAL COMPOSITIONS AND MEDICAL TREATMENTS THEREWITH

RELATED APPLICATION

This is a continuation-in-part of Ser. No. 08/386,957, filed Feb. 10, 1995, now abandoned.

FIELD OF THE INVENTION

This invention relates to verotoxin pharmaceutical compositions and to methods of treating mammalian neoplasia, particularly, brain, ovarian and skin cancers, therewith.

BACKGROUND TO THE INVENTION

Bacteriocins are bacterial proteins produced to prevent the growth of competing microorganisms in a particular biological niche. A preparation of bacteriocin from a particular strain of *E. coli* ($HSC_{10}$) has long been shown to have anti-neoplastic activity against a variety of human tumour cell lines in vitro (1,2). This preparation, previously referred to as PPB (partially purified bacteriocin (2)) or ACP (anti-cancer proteins (2)) was also effective in a murine tumour model of preventing metastases to the lung (2).

Verotoxins, also known as SHIGA-like toxins, comprise a family known as Verotoxin 1, Verotoxin 2, Verotoxin 2c and Verotoxin 2e of subunit toxins elaborated by some strains of *E. coli* (3). These toxins are involved in the etiology of the hemolytic uremic syndrome (3,4) and haemorrhagic colitis (5). Cell cytotoxicity is mediated via the binding of the B subunit of the holotoxin to the receptor glycolipid, globotriaosylceramide, in sensitive cells (6).

The verotoxin family of *E coli* elaborated toxins bind to the globo series glycolipid globotriaosylceramide and require terminal gal α-1–4 gal residue for binding. In addition, VT2e, the pig edema disease toxin, recognizes globotetraosylceramide ($Gb_4$) containing an additional β 1–3 linked galNac residue. These glycolipids are the functional receptors for these toxins since incorporation of the glycolipid into receptor negative cells renders the recipient cells sensitive to cytotoxicity. The toxins inhibit protein synthesis via the A subunit—an N-glycanase which removes a specific adenine base in the 28S RNA of the 60S RNA ribosomal subunit. However, the specific cytotoxicity and specific activity is a function of the B subunit. In an in vitro translation system, the verotoxin A subunit is the most potent inhibitor of protein synthesis yet described, being effective at a concentration of about 8 pM. In the rabbit model of verocytotoxemia, pathology and toxin targeting is restricted to tissues which contain the glycolipid receptor and these comprise endothelial cells of a subset of the blood vasculature. Verotoxins have been strongly implicated as the etiological agents for hemolytic uremic syndrome and haemorrhagic colitis, microangiopathies of the glomerular or gastrointestinal capillaries respectively. Human umbilical vein endothelial cells (HUVEC) are sensitive to verotoxin but this sensitivity is variable according to cell line. Human adult renal endothelial cells are exquisitely sensitive to verotoxin in vitro and express a correspondingly high level of $Gb_3$. However, HUS is primarily a disease of children under three and the elderly, following gastrointestinal VTEC infection. It has been shown that receptors for verotoxin are present in the glomeruli of infants under this age but are not expressed in the glomeruli of normal adults. HUVEC can be sensitized to the effect of verotoxin by pretreatment by tumour necrosis factor which results in a specific elevation of $Gb_3$ synthesis (7,8). Human renal endothelial cells on the other hand, although they express high levels of $Gb_3$ in culture, cannot be stimulated to increase $Gb_3$ synthesis (8). It has been suggested that the transition from renal tissue to primary endothelial cell culture in vitro results in the maximum stimulation of $Gb_3$ synthesis from a zero background (9). We therefore suspect that HUS in the elderly is the result of verotoxemia and a concomitant stimulation of renal endothelial cell $Gb_3$ synthesis by some other factor, eg. LPS stimulation of serum α TNF. Thus under these conditions, the majority of individuals (excepting the very young) would not be liable to VT induced renal pathology following systemic verotoxemia.

It has also been shown that the verotoxin targets a sub-population of human B cells in vitro (10). These $Gb_3$ containing B cells are found within the germinal centres of lymph nodes (11). It has been proposed that $Gb_3$ may be involved in a germinal centre homing by CD19 positive B cells (12) and that $Gb_3$ may be involved in the mechanisms of antigen presentation (13).

Elevated levels of $Gb_3$ have been associated with several other human tumours (14–16), but ovarian tumours have not been previously investigated. $Gb_3$ is the $p^k$ blood group antigen (17). Tissue surveys using anti-$p^k$ antisera have shown that human ovaries do not express this glycolipid (18, 19). Sensitivity to VT1 cytotoxicity in vitro has been shown to be a function of cell growth, the stationary phase cells being refractile to cytotoxicity (20). The sequence homology between the receptor binding B subunit and the human α2-interferon receptor and the B cell marker CD19 suggests that expression of $Gb_3$ is involved in the mechanism of α2-interferon and CD19 signal transduction (12). On surface ligation, $Gb_3$ has been shown to undergo a retrograde intracellular transport via the rough endoplasmic reticulum to the nuclear membrane (21).

The astrocytoma is the most common primary human brain tumour. The majority of astrocytomas are malignant neoplasms which infiltrate diffusely into regions of normal brain. Despite the advent of promising adjuvant therapies and drugs which have impacted positively on patient survival in other tumor types in recent times, no such promising therapy has yet been found for the patient with a malignant astrocytoma. The median survival for patients with glioblastoma multiforme, the most malignant form of astrocytoma, is approximately 12 months and accordingly, it is imperative that new therapeutic treatments for malignant astrocytomas be found.

VTs consist of a 30 kDa enzymatic A subunit which is capable of inhibiting protein synthesis. The A subunit is noncovalently associated with a pentameric 7 kDa B subunit array which binds to $Gb_3$.

In addition to the cytotoxic effects of VTs on a wide range of cells by the A subunit inhibition of protein synthesis, recent evidence suggests that VT1. and the receptor binding B subunit alone, also induce morphological changes and DNA fragmentation characteristic of apoptosis in $Gb_3$-positive cells (22, 23).

REFERENCE LIST

The present specification refers to the following publications, each of which is incorporated herein by reference:

1. Farkas-Himsley, H. and R. Cheung. Bacterial Proteinaceous Products (bacteriocins as cytotoxic agents of neoplasia). *Cancer Res.* 36:3561–3567, (1976).
2. Hill, R. P. and H. Farkas-Himsley. Further studies of the action of a partially purified bacteriocin against a murine fibrosarcoma. *Cancer Res.* 51:1359–1365 (1991).

3. Karmali, M. A. Infection by Verocytotoxin-producing *Escherichia coli. Clin. Microbiol. Rev.* 2:15–38 (1989).
4. Karmali, M. A., M. Petric, C. Lim, P. C. Fleming, G. S. Arbus and H. Lior, 1985. The association between hemolytic uremic syndrome and infection by Verotoxin-producing *Escherichia coli*, J. Infect. Dis. 151:775.
5. Riley, L. W., R. S. Remis, S. D. Helgerson, H. B. McGee, J. G. Wells, B. R. Davis, R. J. Hebert, E. S. Olcott, L. M. Johnson, N. T. Hargrett, P. A. Blake and M. C. Cohen. Haemorrhagic colitis associated with a rare *Escherichia coli* serotype. *N. Engl. J. Med.* 308:681 (1983).
6. Lingwood, C. A., Advances in Lipid Research. R. Bell, Y. A. Hannun and A. M. Jr. *Academic Press.* 25:189–211 (1993).
7. van de Kar, N. C. A. J., L. A. H. Monnens, M. Karmali and V. W. M. van Hinsbergh. Tumour necrosis factor and interleukin-1 induce expression of the verotoxin receptor globotriaosyl ceramide on human endothelial cells. Implications for the pathogenesis of the Hemolytic Uremic Syndrome. *Blood.* 80:2755, (1992).
8. Obrig T., C. Louise, C. Lingwood, B. Boyd, L. Barley-Maloney and T. Daniel. Endothelial heterogeneity in Shiga toxin receptors and responses. *J. Biol. Chem.* 268:15484–15488 (1993).
9. Lingwood, C. A. Verotoxin-binding in human renal sections. *Nephron.* 66:21–28 (1994).
10. Cohen, A., V. Madrid-Marina, Z. Estrov, M. Freedman, C. A. Lingwood and H. M. Dosch. Expression of glycolipid receptors to Shiga-like toxin on human B lymphocytes: a mechanism for the failure of long-lived antibody response to dysenteric disease. *Int. Immunol.* 2:1–8 (1990).
11. Gregory, C. D., T. Turz, C. F. Edwards, C. Tetaud, M. Talbot, B. Caillou, A. B. Rickenson and M. Lipinski. 1987. Identification of a subset of normal B cells with a Burkitt's lymphoma (BL)-like phenotype. *J. Immunol.* 139:313–318 (1987).
12. Maloney, M. D. and C. A. Lingwood, CD19 has a potential CD77 (globotriaosyl ceramide) binding site with sequence similarity to verotoxin B-subunits: Implications of molecular mimicry for B cell adhesion and enterohemorrhagic *E. coli* pathogenesis. *J. Exp. Med.* 180: 191–201,(1994).
13. Maloney, M. and C. Lingwood. Interaction of verotoxins with glycosphingolipids. *TIGG.* 5:23–31 (1993).
14. Li, S. C., S. K. Kundu, R. Degasperi and Y. T. Li. Accumulation of globotriaosylceramide in a case of leiomyosarcoma. *Biochem. J.* 240:925–927 (1986).
15. Mannori G., O. Cecconi, G. Mugnai and S. Ruggieri. Role of glycolipids in the metastatic process: Characteristics neutral glycolipids in clones with different metastatic potentials isolated from a murine fibrosarcoma cell line. *Int. J. Cancer.* 45:984–988 (1990).
16. Ohyama, C., Y. Fukushi, M. Satoh, S. Saitoh, S. Orikasa, E. Nudelman, M. Straud and S. I. Hakomori. Changes in glycolipid expression in human testicular tumours. *Int. J. Cancer.* 45:1040–1044, (1990).
17. Naiki, M. and D. M. Marcus. Human erythrocyte P and $P^k$ blood group antigens: Identification as glycosphingolipids. *Biochem. Biophys. Res. Comm.* 60:1105–1111, (1974).
18. Pallesen, G. and J. Zeuthen. Distribution of the Burkitt's-lymphoma-associated antigen (BLA) in normal human tissue and malignant lymphoma as defined by immunohistological staining with monoclonal antibody 38:13. *J. Cancer Res. Clin. Oncol.* 113:78–86 (1987).
19. Kasai, K., J. Galton, P. Terasaki, A. Wakisaka, M. Kawahara, T. Root and S. I. Hakomori. Tissue distribution of the Pk antigen as determined by a monoclonal antibody. *J. Immunogenet.* 12:213 (1985).
20. Pudymaitis, A. and C. A. Lingwood. Susceptibility to verotoxin as a finction of the cell cycle. *J. Cell Physiol.* 150:632–639 (1992).
21. Sandvig, K., O. Garred, K. Prydz, J. Kozlov, S. Hansen and B. van Deurs. Retrograde transport of endocytosed Shiga toxin to the endoplasmic reticulum. *Nature.* 358:510–512 (1992).
22. Mangeney, M., Lingwood, C. A., Caillou, B., Taga, S., Tursz, T. and Wiels, J. Apoptosis induced in Burkitt's lymphoma cells via $Gb_3$/CD77, a glycolipid antigen. *Cancer Res.* 53: 5314–5319, 1993.
23. Sandvig, K. and van Deurs, B. Toxin-Induced Cell Lysis: Protection by 3-Methyladenine and Cycloheximide. Exp *Cell Res.* 200: 253–262, 1992.
24. Ramotar, K., Boyd, B., Tyrrell, G., Gariepy, J., Lingwood, C. A. and Brunton, J. characterization of Shiga-like toxin 1 B subunit purified from overproducing clones of the SLT-1 B cistron. *Biochem. J.* 272: 805–811, 1990.
25. Costello, R. and Delmaestro, R., Human cerebral endothelium; Isolation and characterization of cell drived from microvessels of non-neoplastic and malignant glial tissue. *J. Neuro-oncol.* 8:231–243, 1990.
26. Pintus, C., Ransom, J. and Evans, C. Endothelial cell growth supplement: a cell cloning factor that promotes the growth of monoclonal antibody producing hybridoma cells. *J. Immunological Methods.* 61:195–200, 1983.
27. Rutka J. T., Kleppe-Hoifodt H., Emma D. A., Giblin J. R., Dougherty D. V., McCulloch J. R., DeArmond S. J. and Rosenblum M. L., Characterization of normal human brain cultures: Evidence for the outgrowth of leptomeningeal cells. *Laboratory Investigation* 55: 71–85, 1986.

Although anti-neoplastic effects of bacterial preparations have been known for over twenty years, the neoplastic effect of verotoxin per se has, to-date, remained unknown. As a result of extensive investigations, we have discovered that verotoxin, particularly Verotoxin 1, is an active component within the ACP and that purified Verotoxin 1 has potent anti-neoplasia effect in vitro and in vivo. Most surprisingly, we have found effective in vivo anti-cancer treatments of human beings commensurate with non-toxic administered dosages.

SUMMARY OF THE INVENTION

It is an object of the present invention to provide a pharmaceutical composition for the treatment of mammalian neoplasia and, particularly, brain, skin cancer and ovarian cancer.

It is a further object of the present invention to provide a method of treating mammalian neoplasia, particularly, skin, brain and ovarian cancers.

Accordingly, in one aspect the invention provides a pharmaceutical composition for the treatment of mammalian neoplasia comprising a non-lethal anti-neoplasia effective amount of a verotoxin, preferably, verotoxin 1, or the pentameric B subunit of verotoxin and a suitable pharmaceutically acceptable diluent, adjuvant or carrier therefor.

The invention preferably provides a pharmaceutical composition and method of treatment for mammalian skin cancers, brain cancers and ovarian cancer.

In a further aspect the invention provides a process for the manufacture of a pharmaceutical composition for the treatment of mammalian neoplasia, said process comprising admixing verotoxin or the pentameric B subunit of verotoxin with a pharmaceutically acceptable carrier, adjuvant or diluent therefor.

The present invention provides selective, specific cancer treatments wherein verotoxin or the pentameric B subunit of verotoxin selectively binds with $Gb_3$ in $Gb_3$-containing cells. This is in contrast to the use of broad spectrum anti-neoplastic agents such as most chemotherapeutic agents, in that non-$Gb_3$ containing cells are not affected by verotoxin. The present invention thus provides a most beneficial, cell-selective, therapeutic treatment.

The treatment is of value against cutaneous T-cell lymphomas, particularly, Mycosis Fungoides, sezary syndrome and related cutaneous disease lymphomatoid papilosis. For example, Mycosis fungoides lesions in humans have been cleared without any observed adverse systemic effects by the application of VT1 (5 ng in 2 ml. solution) by interdermal injection in patients.

In a further aspect, the invention provides a method of treating mammalian neoplasia comprising treating said mammal with a non-lethal anti-neoplasia effective amount of a verotoxin, preferably Verotoxin 1 or the pentameric B subunit of verotoxin.

The verotoxin or its B subunit may be administered to the patient by methods well-known in the art, namely, intravenously, intra-arterially, topically, subcutaneously, by ingestion, intra-muscular injection, inhalation, and the like, as is appropriately suitable to the disease. For treatment of a skin cancer, sub-cutaneous application is preferred.

In the practice of the present invention, Verotoxin 1 has been injected intramuscularly into a patient with advanced ovarian carcinoma. No adverse affects were monitored on lymphocyte or renal function and a serum tumour marker was found to continue to rise when the patient was treated with relatively high doses of Verotoxin 1. This tumour was refractory to all conventional cancer therapies. No effect was found on hemoglobin levels.

The verotoxin or its B subunit is, typically, administered in a suitable vehicle in which the active verotoxin or B subunit ingredient is either dissolved or suspended in a liquid, such as serum to permit the verotoxin to be delivered for example, in one aspect from the bloodstream or in an alternative aspect sub-cutaneously to the neoplastic cells. Alternative, for example, solutions are, typically, alcohol solutions, dimethyl sulfoxide solutions, or aqueous solutions containing, for example, polyethylene glycol containing, for example, polyethylene glycol 400, Cremophor-EL or Cyclodextrin. Such vehicles are well-known in the art, and useful for the purpose of delivering a pharmaceutical to the site of action.

Several multi-drug resistant cell lines were found to be hypersensitive to Verotoxin 1. For example, multidrug resistant ovarian cancer cell lines SKVLB and SKOVLC were more sensitive to VT cytotoxicity than corresponding non-multidrug resistant ovarian cancer cell line SKOV3. Such an observation indicates the possible beneficial effect for patients bearing the SKVLB cell line cancer than those with the SKOV3 cell line under VT treatment. Further, our observed binding of VT1 to the lumen of blood vessels which vascularize the tunour mass, in addition to the tumour cells per se, may result in an anti-angiogenic effect to augment the direct anti-neoplastic effect of verotoxin.

A series of human $Gb_3$ containing astrocytoma cell lines were tested for sensitivity to VT. Although all cells were sensitive, the sensitivity varied over a 5000-fold range despite approximately equivalent $Gb_3$ levels. We have found that treatment of the least sensitive cell line with sodium butyrate initiated a 5000-fold increase in VT sensitivity concomitant with an alteration in intracellular VT targeting.

Thus, we have also found that the efficacy of verotoxin and its B subunit may be significantly enhanced by a prior treatment of the neoplastic cells with a sensitizer, such as sodium butyrate.

BRIEF DESCRIPTION OF THE DRAWINGS

In order that the invention may be better understood preferred embodiments will now be described, by way of example only, with reference to the accompanying drawings wherein.

DETAILED DESCRIPTION OF THE INVENTION

Experimental

Figure 1:
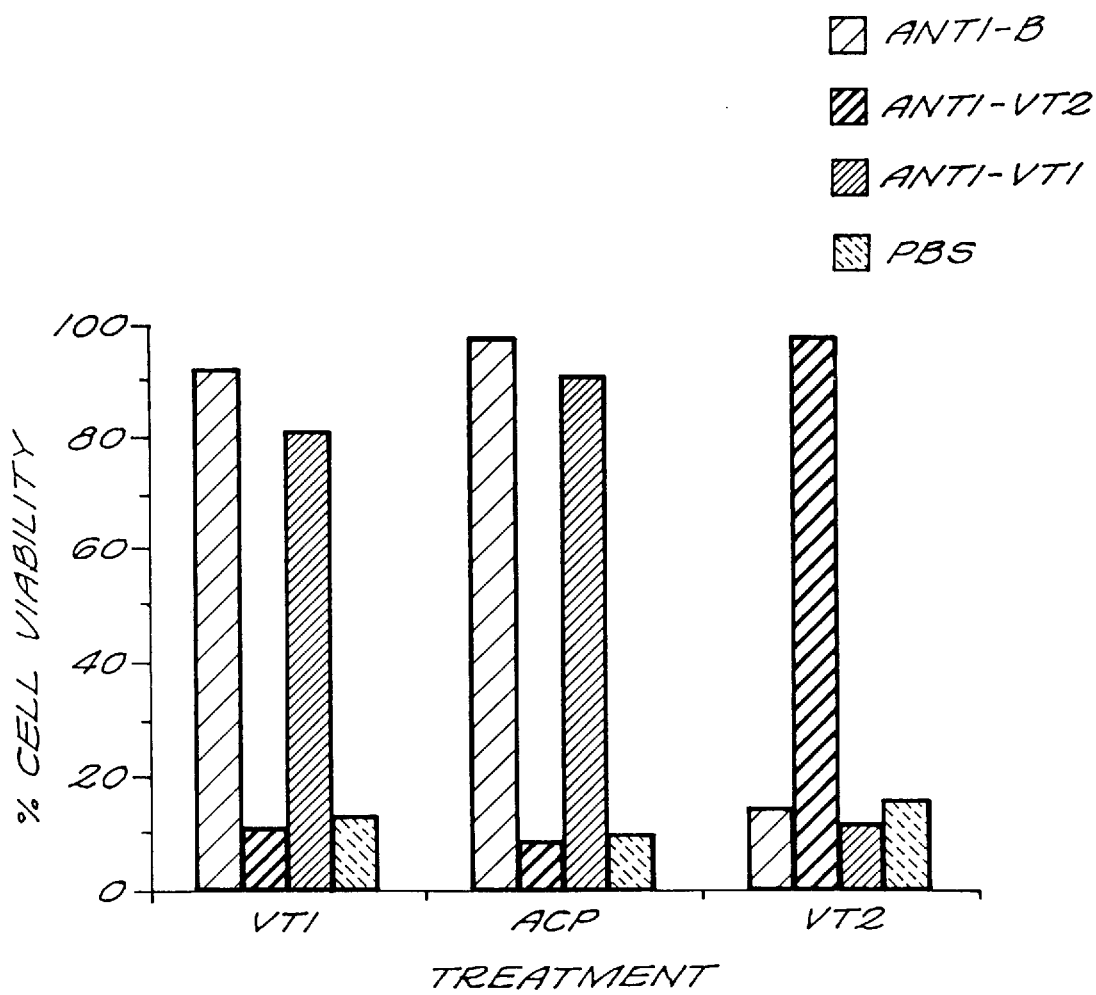
FIG. 1 shows the selective neutralization of ACP cytotoxicity by anti VT1 and or anti VT1 B subunit but not by anti VT2 antibodies as determined by cell density measurement after 48 hours.

The isolation and purification of verotoxins VT1, VT2 and VT2c have been earlier described.

Verotoxin 1 was prepared genetically from the high expression recombinant *E. coli* pJB28, *J. Bacteriol* 166:375 and 169:4313. The generally protein purification procedure described in *FEMS Microbiol. Lett.* 41:63, was followed.

Verotoxin 2 was obtained from R82, *Infect. Immun.* 56:1926–1933; (1988); and purified according to *FEMS Microbiol. Lett.* 48:379–383 (1987).

Verotoxin 2c was obtained from a clinical strain E32511 and purified according to *FEMS Microbiol. Lett.* 51:211–216 (1988).

VT1 B subunit was prepared according to Ramotar (24). VTs were aliquoted in PBS and stored at 70° C. The appropriate dilution for the treatment of astrocytoma cell lines was prepared freshly in media and added to the cells.

Purification of VT1 from JB28

Pellet Preparation may be conducted as follows:

1. Prepare 6×1L LB broth in 3×5L jugs (media) and autoclave. Add carbenicillin to give a 100 μg/ml final conc. when cool.
2. Seed at least 6 ml of penassay (tubes in cold room) +100 μg/ml carbenicillin with JB28 and incubate O/N @37° C.
3. Seed jugs (1 ml seed/liter broth) next morning and incubate for 24 hours at 37° C. at 200 rpm (vigorous shaking).
4. Spin down bugs at 9K for 15 min. at 4° C. and scrape pellet into a freezer bag for future use. Freeze at −70° C.

Preparation of Crude Toxin Extract:

1. Retrieve pellet and dump into beaker. Resuspend in 400 ml of PBS containing 0.1 mg/ml polymyxin B, 50 mg PMSF using a blender. Blend thoroughly then sonicate on ice for −1 minute to disperse further.
2. Incubate in shaking incubator, 200 rpm, or with vigorous stirring @37° C. for 1 hour.
3. Spin down cells @9K for 15 minutes.
4. Pour off supernatant and keep. Resuspend pellet in 400 ml PBS with 0.1 mg/ml polymyxin B and PMSF. Blend and sonicate as before.
5. Incubate with vigorous shaking/stirring at 37° C. for 1 hour.
6. Spin at 10K for 15 minutes and save supernatant.
7. The supernatants should be quite yellow and the bacterial pellet should become more fine and diffuse with each extraction step.
8. Filter the combined supernatants through whatman filter paper than through a glass fibre filter to clarify. This step is optional, but will greatly speed the concentration step.
9. Amicon the combined supernatants at 70 psi (max.) using a YM10 membrane (takes about 200 hours) to concentrate to <50 ml.

Chromatography:

Hydroxylapatite

1. Equilibrate hydroxylapatite column with 10 mM K or Na phosphate (several column volumes).
2. Load sample and wash with equilibration buffer until absorbance of effluent is negligible.
3. Add 2 column volumes (150 ml) of 100 mM K phosphate (until yellow-coloured fractions emerge) and collect 3 ml fractions.
4. Wash column with 500 mM K phosphate and re-equilibrate with 10 mM K phosphate. Add 0.05% sodium azide.

Chromatofocussing

5. Measure fractions ($A_{280}$) and Pool peak fractions from HA.
6. Dialyse against 2L 0.025M imidazole-HCI pH 7.4 O/N. Also equilibrate the chromatofocussing column O/N with the same (300 ml).
7. Load sample and follow with 400 ml polybuffer-HCI pH 5.0 (50 ml polybuffer 74+350 ml $dH_2O$, a 1:7 dilution, -pH to 5.0 with HCI). NOTE: make sure the sample is equilibrated to the temperature that the column will be run at (usually room temperature) prior to loading. If the column is to be run at 4° then buffers must be pH'd at 4° C. and the column equilibrated at this temperature.
8. Collect 1 ml fractions and test them for $A_{280}$ and pH.
9. Plot the $A_{280}$ and pool peak fractions at about pH 6.8 for VT-1 (pool side peaks separately).
10. Clean column with 100 ml 1M NaCl. if really dirty follow with 100 ml 1M HCI, but quickly equilibrate column with imidazole. Store column in 20% ethanol in 25 mM imidazole.

Cibachron blue

11. Equilibrate cibachron blue with 10 mM Na phosphate buffer, pH 7.2 (100 ml).
12. Load sample directly from CF and follow with 60 ml of same buffer.
13. Elute with 0.5M NaCl in above buffer and collect fractions.
14. Test fractions for $A_{280}$ and cytotoxicity and pool appropriate ones.
15. Clean column with 25 ml each of 8M Urea in wash buffer and 1M NaCI in wash buffer.
16. Reequilibrate column with 10 mM phosphate containing 0.1% azide.
17. Dialyse peak fractions against wash buffer with one change.
18. Lyophilize and resuspend in 1 ml $dH_2O$.
19. Do protein assay and run SDS-PAGE to check purity.

Solutions:

| | |
|---|---|
| HA column | |
| potassium phosphate buffer (0.5M stock) | |
| 17.42 g $K_2HPO_4$<br>6.8 g $KH_2PO_4$ | up to 300 ml with dH2O<br>pH 7.2 with KOH |
| CF column | |
| imidazole buffer | |
| 0.851 g/500 ml $H_2O$<br>pH 7.4 with HCI | |
| CB column | |
| sodium phosphate buffer (Wash buffer—WB) | |
| 0.71 g/500 ml $Na_2HPO_4$<br>pH 7.2 with HAc<br>degas | |
| Elution buffer | Cleaning Buffers |
| 2.922 g NaCI/100 ml WB | 12.012 g Urea/25 ml WB<br>1.461 g NaCI/25 ml WB |

Purification of VT2 from R82

Pellet Preparation:

1. Prepare 3×2L penassay broth (Antibiotic Meida 3, DIFCO; pH 7.0) in 3×5L jugs and autoclave at 121° C.

for 20 minutes. Allow broth to cool to room temperature before use.
2. Seed minimum 3×2 ml of penassay broth containing 75 μg/ml carbenicillin (Disodium salt, SIGMA) with R82 and incubate overnight at 37° C., with shaking.
3. Add 50 μg/ml carbenicillin to each of the 5L jugs (from step 1). Seed each jug with 2 ml of seed (step 2) and incubate for 24 hours at 37° C. with shaking of approximately 120 rpm.
4. Heat incubator to 45° C. and incubate for 30 minutes.
5. Reduce temperature to 37° C. and incubate for another 3 hrs.
6. Spin down culture solution at 9,000×g for 15–20 min at 4° C. Discard supernatant and store pellets at −20° C.

Preparation of Crude Toxin Extract:
1. Resuspend pellets in 100 ml of PBS (phosphate buffered saline, OXOID; pH 7.3).
2. Add 0.3 mg/ml PMSF (phenylmethyl-sulfonyl fluoride, SIGMA) dissolved in 0.5 ml acetone to pellet solution. Let acetone evaporate. Sonicate on ice at highest output possible for 5 min or until an homogeneous solution is obtained.
3. Spin down cell at 9,000×g at 4° C. for 20 min. Discard pellets.
4. Concentrate supernatants using ultrafiltration (Model 8400 standard infiltration cell, AMICON) with $N_2$ no higher than 70 psi and using a 10,000 MW cutoff membrane filter (YM10 membrane, AMICON).
5. Using 12–14,000 MW cutoff tubing (SPECTRAPOR) (now and in all dialysis steps), dialyse toxin solution against 4L of 10 mM potassium phosphate overnight, with stirring at 4° C.

Chromatography:
Hydroxylapatite (HA)
1. Equilibrate hydroxylapatite column (BSA binding capacity: 32 mg/g, approximately 113 ml volume; CALBIOCHEM (BEHRING DIAGNOSTICS)) with 2 column volumes of 10 mM potassium phosphate.
2. Load sample and follow with 1 column volume 10 mM potassium phosphate.
3. Add 2 column volumes of 200 mM potassium phosphate and collect 2 ml fractions. The fractions containing the toxin should be coloured differently from the other fractions.
4. Wash column with 1 column volume of 500 mM potassium phosphate and reequilibrate with 1 column volume of 10 mM potassium phosphate. Add azide to the top of the column for storage.

Chromatofocussing (CF)
5. Pool peak fractions from HA column either by colour or by cytotoxicity test on Vero cells (10-fold dilutions).
6. Dialyse pooled fractions against 4L 0.025M Histidine-HCl pH 6.2 (SIGMA) overnight. Also equilibrate the chromatofocussing column (PBE (polybuffer exchanger) 94, 1.5 cm diameter, 57 ml volume; PHARMACIA) overnight with the same buffer (300 ml).
7. Loan sample and follow with 400 ml polybuffer-HCl pH 4.0 (50 ml polybuffer 74 (PHARMACIA) +350 ml $dH_2O$—pH to 4.0 with HCl).
8. Collect 2 ml fractions and test the pH of each fraction. Once the pH has dropped to 3.95, stop collecting fractions. Test the fractions using absorbance of 280 nm or by cytotoxicity on Vero cells (10-fold dilutions).
9. Pool peak fractions, and return pH to 7.0 using 1N NaOH.
10. Clean column with 200 ml 1M NaCl. If dirty follow with 100 ml 1M HCl, but quickly equilibrate column with 0.025M imidazole, otherwise equilibrate with 24% $EtOH-H_2O$.

Cibachron blue (CB)
11. Equilibrate cibachron blue (2 cm diameter, 82 ml volume, PIERCE) with 100 ml of 10 mM sodium phosphate buffer (wash buffer).
12. Load sample and follow with 60 ml of wash buffer.
13. Elute with 0.5M NaCl in wash buffer and collect 2 ml fractions.
14. Test fractions for absorbance at 280 nm using the elution buffer as a blank and cytotoxicity on Vero cells and pool appropriate fractions.
15. Clean column with 25 ml each of 8M Urea in wash buffer and 1M NaCl in wash buffer.
16. Reequilibrate column with 100 ml of wash buffer and add azide to the top of the column for storage.
17. Dialyse peak fractions against 4L 0.01M Tris-CL (pH 7.0, SIGMA).
18. Lyophilize sample and resuspend in 1–2 ml $dH_2O$ (OPTIONAL).
19. Do protein assay (BCA Protein assay reagent, PIERCE) and rune SDS-PAGE gel (Schagger, H. and von Jagow, G.; Analytical Biochem 166, 368–379 (1987): 10% T table 2; first line table 3) to check purity.

Solutions:

HA Column potassium phosphate buffer (0.5M stock)

| | |
|---|---|
| 17.42 g $K_2HPO_4$ | up to 300 ml with $dH_2O$ |
| 6.8 g $KH_2PO_4$ | pH 7.2 with KOH |

CF column

Histidine buffer (0.025M)

2.0 g/500 ml $H_2O$
pH 6.2 with HCl

CB column

Sodium phosphate buffer (Wash buffer—WB)

0.71 g/500 ml $Na_2HPO_4$
pH 7.2 with HAc
degas

| Elution buffer (0.5M) | Cleaning Buffers |
|---|---|
| 2.922 g NaCl/100 ml WB | 12.01 g Urea/25 ml WB |
| | 1.46 NaCl/25 ml WB |

0.01M Tris 4.84 g Trizma Base
4 L $ddH_2O$
pH to 7.2 with HCl

Purification of VT2c from E32511
Pellet Preparation:
1. Prepare 3×2L penassay broth (Antibiotic Media 3, DIFCO; pH 7.0) in 3×5L jugs and autoclave at 121° C. for 20 minutes. Allow broth to cool to room temperature before use.
2. Seed minimum 3×2 ml of penassay broth with E32511 and incubate overnight at 37° C.
3. Add 0.2 μg/ml Mitomycin C (1 ml of 0.4 mg/ml) (add 5 ml of $ddH_2O$ to the vial) to each of the 5L jugs (from step 1). Seed each jug with 2 ml of seed (step 2) and incubate for 6 hrs at 37° C. with shaking of approximately 120 rpm. It is very important to stagger the incubation by about 45 min/flask because the toxin begins to deteriorate after 6 hour exposure to Mitomycin C.

4. Spin down culture solution at 9,000×g for 15–20 min at 4° C. Discard supernatant and store pellets at −20° C.

Preparation of Crude Toxin Extract:

1. Resuspend pellets in 150 ml of PBS (Phosphate buffered saline, OXOID; pH 7.3).
2. Add 0.3 mg/ml PMSF (phenylmethyl-sulfonyl fluoride, SIGMA) dissolved in 0.5 ml acetone to pellet solution. Let acetone evaporate. Sonicate on ice at highest output possible for 3 min or until an homogeneous solution is obtained.
3. Add 0.1 mg/ml polymyxin B sulphate (Aerosporin, BURROUGHS WELLCOME INC.; 500,000 units) to solution and incubate with gentle shaking at 37° C. for 1 hr.
4. Spin down cells at 9,000×g at 4° C. for 20 min (to remove all cells and cell debris from solution).
5. Decant supernatant and store at 4° C. Resuspend pellet in 75 ml PBS and add 0.1 mg/ml polymyxin B.
6. Incubate with gentle shaking at 37° C. for 1 hr.
7. Spin down cell at 9,000×g at 4° C. for 20 min and pool supernatants (from step 5). Discard pellets.

The next few steps should preferably be done at 4° C.:

8. Add crystalline ammonium sulphate very slowly, with stirring to pooled supernatants to 30% saturation.
9. Let stir for 20 min and then remove precipitate by centrifugation (10000 g for 10 min).
10. Add crystalline ammonium sulphate very slowly, with stirring to pooled supernatants to 70% saturation.
11. Let stir for 20 min and then centrifuge at 1000 g for 10 min.
12. Resuspend pellet from step 11 in 15 ml of 0.01M Potassium phosphate buffer.
13. Using 12–14,000 MW cutoff tubing (SPECTRAPOR) (now and in all dialysis steps), dialyse toxin solution against 4L of 10 mM potassium phosphate overnight, with stirring at 4° C.

Chromatography:

Hydroxylapatite (HA)

1. Equilibrate hydroxylapatite column (BSA binding capacity: 32 mg/g, approximately 113 ml volume; CALBIOCHEM (BEHRING DIAGNOSTICS)) with 2 column volumes of 10 mM potassium phosphate.
2. Load sample and follow with 1 column volume 10 mM potassium phosphate.
3. Add 2 column volumes of 100 mM–200 mM potassium phosphate and collect 2 ml fractions. The fractions containing the toxin should be coloured differently from the other fractions.
4. Wash column with 1 column volume of 500 mM potassium phosphate and reequilibrate with 1 column volume of 10 mM K phosphate. Add azide to the top of the column for storage.

Chromatofocussing (CF)

5. Pool peak fractions from HA column either by colour or by cytotoxicity test on Vero cells (10-fold dilutions).
6. Dialyse pooled fractions against 4L 0.025M imidazole-HCl pH 7.4 (SIGMA) overnight. Also equilibrate the chromatofocussing column (PBE (polybuffer exchanger) 94, 1.5 cm diameter, 57 ml volume; PHARMACIA) overnight with the same buffer (300 ml).
7. Load sample and follow with 200 ml polybuffer-HCl pH 5.0 (25 ml polybuffer 74 (PHARMACIA) +175 ml dH$_2$O—pH to 5.0 with HCl).
8. Collect 2 ml fractions and test the pH of each fraction. Once the pH has dropped to 5.95, stop collecting fractions. Test the fractions for cytotoxicity on Vero cells (10-fold dilutions).
9. Pool peak fractions.
10. Clean column with 200 ml 1M NaCl. If really dirty follow with 100 mM 1M HCl, but quickly equilibrate column with 0.025M imidazole.

Cibachron blue (CB)

11. Equilibrate cibachron blue (2 cm diameter, 82 ml volume, PIERCE) with 100 ml of 10 mM sodium phosphate buffer (wash buffer).
12. Load sample and follow with 60 ml of wash buffer.
13. Elute with 0.5M NaCl in wash buffer and collect 2 ml fractions.
14. Test fractions for absorbance at 280 nm using the elution buffer as a blank and cytotoxicity on Vero cells and pool appropriate fractions.
15. Clean column with 25 ml each of 8M Urea in wash buffer and 1M NaCl in wash buffer.
16. Reequilibrate column with 100 ml of wash buffer and add azide to the top of the column for storage.
17. Dialyse peak fractions against 4L 0.01M Tris-CL (pH 7.0, SIGMA).
18. Lyophilize sample and resuspend in 1–2 ml dH$_2$O (OPTIONAL).
19. Do protein assay (BCA Protein assay reagent, PIERCE) and run SDS-PAGE gel (Schagger, H. and von Jagow, G.; Analytical Biochem 166, 368–379 (1987): 10% T table 2; first line table 3) to check purity.

Solutions:

HA column potassium phosphate buffer (0.5M stock)

| | |
|---|---|
| 17.42 g K$_2$HPO$_4$ | up to 300 ml with dH$_2$O |
| 6.8 g KH$_2$PO$_4$ | pH 7.2 with KOH |

CF column imidazole buffer (0.025M)

0.851 g/500 ml H$_2$O
pH 7.4 with HCl

CB column sodium phosphate buffer (Wash buffer—WB)

0.71 g/500 ml Na$_2$HPO$_4$
pH 7.2 with HAc
degas

| Elution buffer | Cleaning buffers |
|---|---|
| 2.922 g NaCl/100 ml WB | 12.012 g Urea/25 ml WB |
| | 1.461 g NaCl/25 ml WB |

0.01M Tris 4.84 g Trizma Base
4 L ddH$_2$O
pH to 7.2 with HCl

Affinity purification of verotoxins

500 µg globotriaosyl ceramide in 1 ml chloroform was mixed and dried with 1 g of dried celite. The chloroform was evaporated and the celite suspended in PBS and poured in a column. Crude polymyxin extract 20 ml (25 mg protein) the toxin producing *E. coli* was applied to the column and incubated at room temp for 15 mins. The column was washed with PBS and purified verotoxin eluted with 10 ml 1M Tris pH 9.6. The eluate was neutralized and dialysed. This method is applicable for purification of all verotoxins. (Boulanger, J., Huesca, M., Arab, S and Lingwood, C. A. "Universal method for the facile production of glycolipid/lipid matrices for the affinity purification of binding ligands" Anal Biochem 217: 1–6 [1994])

Preparation of verotoxin 1 doses

VT1 was purified from the *E. coli* strain as previously described which overexpresses the cloned toxin genes. The purified toxin was free of endotoxin contamination. The protein concentration of this batch of verotoxin was determined and the toxin aliquoted and stored at −70° C.

To prepare VT1 doses for patients, VT1 was diluted into injection grade sterile saline containing 0.2% v/v of the patient's own serum. 210 ul of sterile patient serum was added to 10 ml of sterile injection saline and 93.9 ml of purified VT1 (6.7 g/ml) added to give a final toxin concentration of 62.5 ng/ml or 12.5 ng per 0.2 ml. dose. The final toxin preparation was sterile-filtered using a 0.2 mm syringe filter and dispensed in 2 ml aliquots into 10 ml vials. One working vial may be stored at 4° C. and the remaining vials frozen until needed.

FITC labelling of VT1: FITC was added directly to VT1 (in a 1:1, w/w ratio) in 0.5M $Na_2CO_3/NaHCO_3$ conjugated buffer pH 9.5 and the mixture gently rotated for 1.2 hours at room temperature. Free FITC was removed by centricon.

Fluorescent Staining of Sections: Samples of surgically removed ovarian tumours were embedded in OCT compound, flash frozen in liquid nitrogen, and stored at −70° C. until use. Five µm sections of frozen sample were thawed, allowed to dry and stained with FITC-labelled VT1 in PBS (0.5 mg.ml) containing 0.1% BSA for 1 h at room temperature. Sections were extensively washed with PBS and mounted with mounting medium containing DABCO. Sections were observed under a Polyvar fluorescent microscope.

Fluorescent Staining of Cells: Cells growing on coverslips were washed once with PBS, fixed for 2 min at room temperature with 2% formalin rinsed with PBS twice and incubated with FITC-VT1 for 1 h at room temperature. The cells were washed 5 times with PBS, mounted with DABCO and observed under a Polyvar fluorescent microscope.

Quantification of VT1 antitumour activity: SKOV3 (drug sensitive human ovarian cell line), SKOVLC (SKOV3, resistant to Vincristine, and SKOVLB (SKOV3, resistant to Vinblastine) were each grown in α-MEM supplemented with 10% fetal calf-serum and tested for their 10-fold dilution of VTs were tested in triplicate and incubated for 48 h at 37° C. in a humidified atmosphere containing 5% $CO_2$. Cells were then fixed with 2% Formalin, stained with Crystal Violet, and read with ELISA plate reader.

To quantify the anticancer activity of VT1. SKOV3, SKOVLC, and SKOVLB (human ovarian cell line) were incubated with 10-fold dilution of VT1 for 48 h. SKOVLC & SKOVLB (drug resistant cell lines) are more sensitive to VT1 antitumour activity than SKOV3.

Preparation of $^{131}I$-VT1B

This material may be made by the following procedure.

1. Dissolve 20 mg of iodogen in 2.0 ml of chloroform (10 mg/ml). Make a 1:10 dilution by adding 0.25 ml of the 10 mg/ml solution to 2.25 ml chloroform (1 mg/ml).

2. Dispense 20 ul of this dilute solution into a clean, dry sterilized glass tub. Add 500 ul of chloroform and evaporate to dryness under $N_2$.

3. Add 1.5 mg. in 0.66 ml of VT1 B subunit to the test tube.

4. Add 5 MCi of $^{131}I$ sodium iodide in 100 ul. Allow labelling to proceed for 10 mins.

5. Wash a PD-10 column with 25 ml of Sodium Chloride Injection USP.

6. Dilute $^{131}I$-VT1B to 2.5 ml total volume with 1% HSA in Sodium Chloride Injection USP. Load onto PD-10 column. Elute column with 3.5 ml 1% HSA in saline.

7. Measure $^{131}I$ activity of eluant and column to determine LE. Draw up pooled fractions into a syringe with spinal needle attached. Detach spinal needle and attach Millex GV filter.

8. Filter into a sterile 10 ml multidose vial. Note volume filtered and assay vial for $^{131}I$ in dose calibrator. Calculate concentration.

9. Draw up 0.1 ml of $^{131}I$-VT1B and dispense 0.05 ml into each of two 5 ml sterile multidose vials (one for sterility test and one for pyrogen test). Vials already contain 2 ml saline (=1:50 dilution).

10. Determine RCP by PC (Whatman No. 1) in 85% MeOH and by size exclusion HPLC.

11. Conduct sterility and pyrogen tests.

Astrocytoma Cell Lines, Endothelial Cells and Culture Conditions:

Six permanent human malignant astrocytoma cell lines (SF-126, SF-188, SF-539, U 87-MG, U 251-MG, and XF-498) were selected for study. SF-126, SF-188, and SF-539 were kindly provided by Dr. Mark Rosenblum, Henry Ford Hospital. U 87-MG and U 251-MG were kindly provided by Dr. Jan Ponten, University of Uppsala, Sweden; and XF-498 was a gift of Dolores Dougherty, University of California San Francisco. Astrocytoma cells were cultured in alpha-MEM, nonessential amino acids, glutamine, gentamycin, and 10% heat-inactivated fetal bovine serum. The cultures were incubated at 37° C. and equilibrated in 5% $CO_2$ and air. Cells were harvested with 0.25% trypsin (Gibco, Santa Clara, Calif.) in $Ca^{++}$ and $Mg^{++}$ free Hank's balanced salt solution and were subcultured weekly.

Human capillary endothelial cells were isolated after the method of Costello (25) and were derived from samples of normal human brain taken from patients undergoing neurosurgical procedures for epilepsy, trauma, and resection of arteriovenous malformations. The capillary cells were grown as described above in media supplemented with 15 µg/ml endothelial growth factor (Sigma, St. Louis) (26). The endothelial origin of the cells in culture was established by immunocytochemical analysis using anti-human factor-VIII-related antigen antisera (Dako, Santa Barbara, Calif.) as described previously (27).

Approximately $1-5 \times 10^4$ cells were added to 24-well plates and incubated in α-MEM in 5% $CO_2$ at 37° C. After 24 hours, the growth medium was replaced with medium containing various concentrations of the holotoxin VT1 (0, 0.1, 5, 50, and 100 ng/ml). The treated astrocytoma cell lines and endothelial cells were trypsinized and counted at intervals throughout the growth curve. Cell viability was assessed by trypan blue dye exclusion. Cell counts were plotted again time for the various concentrations of VT1 and B subunit. For each time point analyzed, the wells were set-up in triplicate.

For selected cell lines, the B subunit of VT1, VT2, and VT2c was added alone to the astrocytoma cells at same concentrations listed above. In these experiments, a single dose of VT1, VT2, and VT2c was added to confluent astrocytoma cells in microtiter wells. Cell survival at 72 hours was monitored by staining with 0.1% crystal violet, and measuring the optical density at 590 nm using a Dynatek microtiter plate reader.

VT Receptor Analysis of Human Astrocytoma Cells:

Cultured human astrocytoma cells were homogenized in a minimum volume of PBS and extracted with 20 volumes of a 2:1 by volume chloroform:methanol solution. The extract was partitioned against water and the lower phase partitioned again against theoretical upper phase. The lower phase was dried completely and dissolved in a known volume of 2:1 chloroform:methanol. The presence of $Gb_3$ was detected by TLC overlay binding with VT1. Astrocytoma lower phase and standard $Gb_3$ from human kidney each were separated by TLC [(chloroforn:methanol:water= 65:25:4 (v/v/v)]. The TLC plates were dried and blocked with 1% gelatin in water at 37° C. overnight. Then they were washed three times with 50 mm TBS (Tris Buffer Salin) for 5 min and incubated with 0.1 $\mu$g/ml VT1 for 1 hour. After further washing with TBS, the plates were incubated with a mouse monoclonal PH1 and anti-VT1 antibody (2 $\mu$g/ml), followed, after washing, by peroxidase-conjugated goat anti-mouse antibody or peroxidase conjugated goat anti-rabbit antibody as appropriate. Finally, the plates were washed with TBS, and VT1 binding was visualized with 4-chloro-1 naphthol peroxidase substrate. A similar plate was prepared and stained with orcinol carbohydrate spray for comparison.

Nuclear staining with propidium iodide:

SF-539 cells grown on the cover slips overnight were incubated at 37° C. with VT1 B-subunit (50 $\mu$g/ml) for 1.5 hrs or 10 hrs and fixed (with 1% paraformaldehyde for 3 minutes), permeabilized with 0.1% Triton X in 100 mm PBS for 5 min, and stained with 5 $\mu$g/ml propidium iodide (sigma). After extensive wash with 50 mm PBS, the fixed cells were mounted with DABCO (1,4-Diazabicyclo-Octane, sigma), and nuclear staining observed under incident uv illumination.

Flow Cytometry:

Apoptosis of astrocytoma cells, incubated with 10 ng/ml of VT1 for 24–36 hrs in the presence of 10% bovine fetal serum was analyzed on an Epics Profile Analyzer (Coulter Electronics, Pathology, University of Toronto). After treatment, cells were trypsinized and the 200×g centrifuged cell pellet was suspended in 1 ml of hypotonic fluorochrome solution of 50 $\mu$g/ml propidium iodide (sigma) and stained for 30 min at 4 C. To remove RNA prior to staining, cells were treated with 100 ul of 200 ug/ml DNase-free RNase A at 37 C for 30 min. Cell cycle distribution was determined using manual gating. Flow cytometric quantitation of apoptotic cells within the propidium iodide-stained population was performed. Debris and dead cells were excluded on the basis of their forward and side light-scattering properties. Astrocytoma cells grown simultaneously in the absence of VT1 served as controls.

Ultrastructural Analysis of VT-treated Astrocytoma Cells:

Cells were cultivated on a transferable 9 mm cyclopore membrane (0.45 um pore size, Falcon) to form a confluent monolayer and were incubated at 37° C. with VT1 (10 ng/ml). Cells were fixed at room temperature by addition of 1.6% glutaraldehyde to the well and then incubated in 0.066M Sorensen buffer (pH 7.4) containing 1.5% glutaraldehyde for 1 h at 4° C. After 2 h of washing with 0.1M phosphate buffer, cells were post-fixed in 2% osmium tetroxide in the same buffer. After dehydration in graded ethanols and propylene oxide, Epon embedding and uranyl-lead staining were performed. Thin sections were examined in a Philips EM 400 electron microscope and ultrastructural features of apoptosis was analysed.

FIG. 1 relates to the neutralization of ACP cytotoxicity by anti-VT. KHT cell monolayers were incubated with 35 ng/ml ACP from *E.coli* $HSC_{10}$, or 10 pg/ml VT1, VT2 or VT2c in the presence of monoclonal anti-VT1(PH1), monoclonal anti VT2 or polyclonal rabbit antiVT1 B subunit. The cells were incubated for 72 hours at 37° C. and viable adherent cells were detected by fixation and staining with crystal violet. Cytotoxity of VT1 and ACP was completely neutralized in the presence of anti VT1 or anti VT1B subunit (anti-VT2 serum had no effect).

Figure 2:
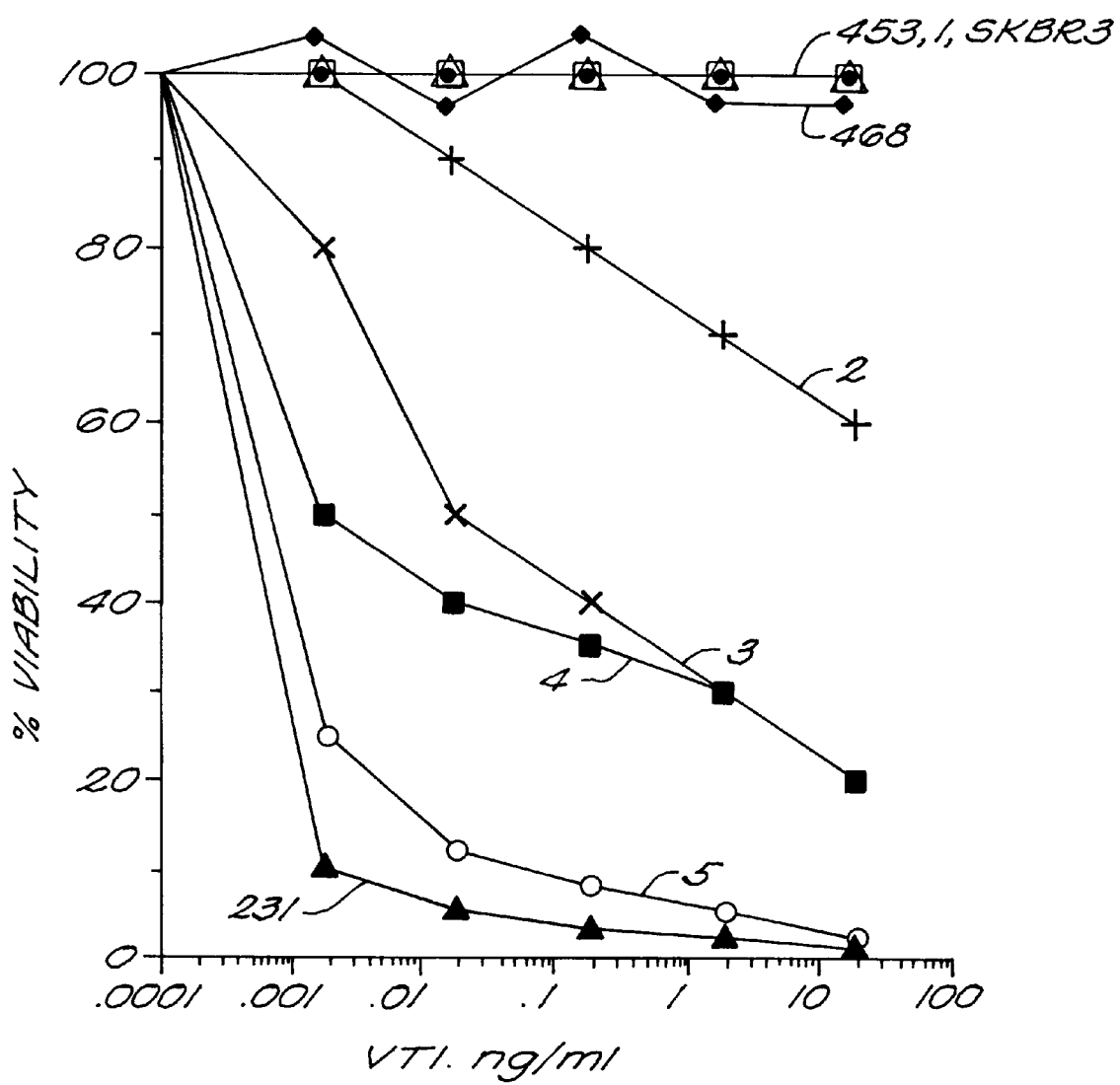
FIG. 2 shows the viability of selected ovarian and breast tumour cell lines to verotoxin concentration.

From measurement of the cytotoxic assay of ACP on vero cells (cells from Africa green monkey kidney that are very sensitive to verotoxin), relative to a pure VT1 standard, it was estimated that the ACP preparation contained 0.05% VT1. This concentration of purified VT1 was as effective as ACP in inhibiting the growth of various tumour cell lines in vitro (FIG. 2). Thus, VT1 mimics the anti-neoplastic effect of ACP in vitro. VT1 was tested for the ability to inhibit the metastases of KHT fibrosarcoma cells in the mouse model as had been previously reported for ACP. The equivalent dose of VT1 was as effective as ACP, reducing the number of lung metastases to background levels, following a primary subcutaneous tumour inoculum (Table 1).

TABLE 1

Response of KHT cells, growing as lung modules, to treatment with VT-1 or ACP.

| GP | TREATMENT | # OF MICE | # OF LUNG NODULES/MOUSE | MEAN | WT LOSS/ GAIN* |
|----|-----------|-----------|--------------------------|------|----------------|
| EXPT 1 | | | | | |
| 1 | Control | 9 | 34, 24, 39, 47, 28, 32, 26, 29, 34 | 32.6 | +5% |
| 2 | ACP-0.25 ug/mouse | 4 | 12, 31, 25, 15 | 20.8 | 0 |
| 3 | ACP-1.0 ug/mouse | 6 | 1, 2, 2, 5, 1 | 2.2 | 0** (1 death) |
| 4 | ACP-4 ug/mouse | 5 | 0, 0, 0, 0, 0 | 0 | −13% |
| 5 | VT-1 0.009 ug/mouse | 5 | 29, 41, 34, 29, 21 | 30.8 | +5% |
| 6 | VT-1 0.036 ug/mouse | 5 | 7, 16, 29, 16, 6 | 14.8 | +5% |
| 7 | VT-1 0.144 ug/mouse | 5 | 1, 4, 2, 3, 1 | 2.2 | +5% |
|  | Control | 4 | 15, 12, 8, 12 | 11.75 | <5% |
| 2 | ACP-2 ug/mouse | 5 | 0, 1, 0, 0, 0 | 0.2 | <5% |
| 3 | VT-1 0.1 ug/mouse | 4 | 0, 0 | 0 | <5%*** |

TABLE 1-continued

Response of KHT cells, growing as lung modules, to treatment with VT-1 or ACP.

| GP | TREATMENT | # OF MICE | # OF LUNG NODULES/MOUSE | MEAN | WT LOSS/ GAIN* |
|---|---|---|---|---|---|
|  |  |  |  |  | (2 deaths) |
| 4 | VT-1B-0.2 ug/mouse | 5 | 13, 14, 9, 7, 19 | 12.4 | <5% |
| 5 | VT-1B-10 ug/mouse | 5 | 8, 3, 9, 11 | 6.8 | <5% |

Mice were treated with VT-1 or ACP(1-p) 1 day after cell injection (1000 KHT cells/mouse i-v).
Lung nodules counted @ 20 days after cell injection.
*Mean change in gp wi-max during 10 days (Expl 1) or 4 days (Expt 2) after VT-1 or ACP injection.
Max wt loss @ days 7–8.
**Death occurred @ days 2–3 after ACP injection
***Deaths occurred @ days 7–8

Figure 5:
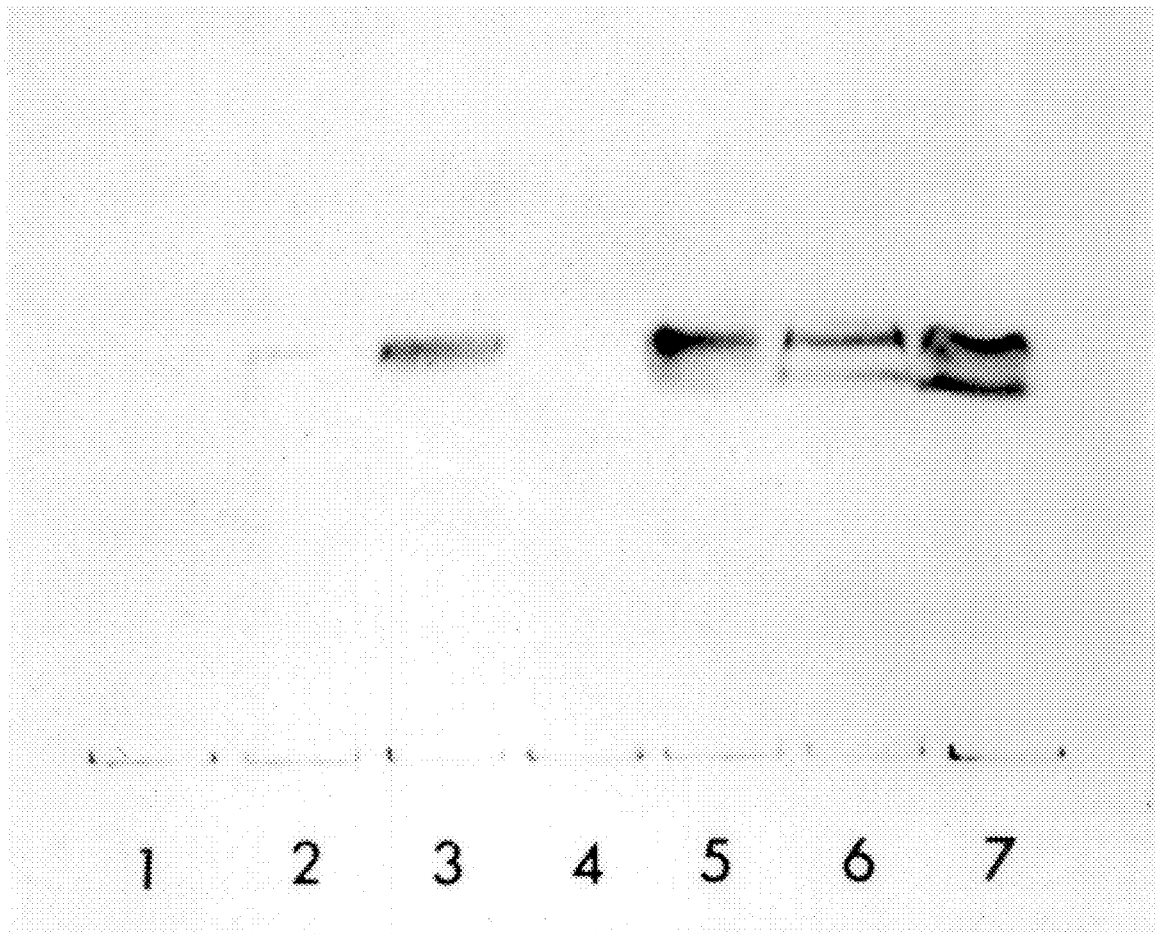
FIG. 5 represents VT thin layer chromatography overlay of selected cell line glycolipids.

Purified VT1 was found to mimic the anti-metastatic effect of ACP on the growth of this tumour from a primary subcutaneous site. Lung metastasis was completely inhibited. Moreover, prior immunization of mice with the purified B-subunit of verotoxin completely prevented any protective effect of ACP when the animals were subsequently treated with the tumour and ACP (Table 2).

TABLE 2

Response of KHT lung nodules, growing to immunized mice, to treatment with VT or ACP

| GP | IMMUNIZATION* | TREATMENT | # OF MICE | # OF LUNG NODULES/ MOUSE | MEAN | WT LOSS/ GAIN* |
|---|---|---|---|---|---|---|
| 1 | None | None | 6 | 34, 47, 53, 62, 43, 52 | 48.5 | <5% |
| 2 | None | VT-1 −0,2 ug/mouse | 5 | | | 5 deaths (dy 6–8)** |
| 3 | None | ACP-2.0 ug/mouse | 5 | 0, 1, 2, 0, 0 | 0.6 | −8% |
| 4 | VT-1B + FA | None | 5 | 43, 40, 47, 43, 23 | 39.2 | −6% |
| 5 | VT-1B + FA | VT-1 −0,2 ug/mouse | 6 | 26, 44, 49, 21, 43, 37 | 36.7 | <5% |
| 6 | VT-1B + FA | ACP-2.0 ug/mouse | 6 | 50, 38, 33, 41, 48, 50 | 43.3 | <5% |
| 7 | FA only | None | 5 | 44, 60, 19, 25, 40 | 37.6 | <5% |
| 8 | FA only | VT-1 −0,2 ug/mouse | 5 | | | 5 deaths (dy 6–8)*** |
| 9 | FA only | ACP-2.0 ug/mouse | 5 | 1, 1, 2, 1, 0 | 1 | |

Mice were treated with VT-1 or ACP(i-p) 1 day after cell injection (1000 KHT cells/mouse). Lung nodules counted @ 20 days after cell injection (i-v).
*Immunization was 2 injections of VT-1B (10 ug/mouse +/− Freund's Adjuvant (FA) given (i-p) 4 weeks and 2 weeks before cell injection.
**Mean change in gp wt - max during 13 days. Maximum weight loss @ day 7–8.

ACP was tested for glycolipid binding by TLC overlay using monoclonal anti-VT1 or anti-VT2c. Anti-VT1 shows extensive binding of a component within the ACP preparation to globotriaosylceramide and galabiosyl ceramide (FIG. 3). This binding specificity is identical to that reported for purified VT1(8). No binding component reactive with anti-VT2 was detected. In FIG. 3 anti VT antibodies were used to detect binding to the immobilized glycolipids. Arrows indicate position of standard (from the top) galabiosyl ceramide, globotriaosyl ceramide and globotetraosyl ceramide. Panel 1-detection using anti VT1, panel 2-detection using anti VT2c.

VT1 demonstrated in vitro activity against a variety of ovarian carcinoma cell lines. A large number of primary human ovarian tumour biopsies were screened for the expression of $Gb_3$ via TLC overlay using purified VT1. It was found that $Gb_3$ was barely detectable in normal ovary tissue, whereas in all cases a significant increase in expression of $Gb_3$ was observed in the ovarian carcinoma. Similarly, elevated levels of $Gb_3$ were found in acites tumour and in tumours that had metastized to the omentum, (FIG. 4) which defines lane 1, ovarian omentum metastasis; lane 2: tumour biopsy; lane 3, tumour biopsy; lanes 3–6, normal ovary; lane 7, human kidney $Gb_3$ standard. Surprisingly, we have found that multi-drug resistant variants of ovarian tumour cell lines were considerably more sensitive to VT1 cytotoxicity than the drug sensitive parental cell line (FIGS. 2, 5 and 6). Similar effects had been observed for ACP. FIG. 2 shows human ovarian tumour cell lines sensitive to ACP tested for VT sensitivity. Human ovarian and breast tumour derived cell lines were tested for VT1 sensitivity wherein ovarian 1, 2, 3, 4 and 5 are denoted □, +, x, ■ and o respectively, and breast-SKBR3, 468♦, 453☺, 231▲.The cell lines 1-ovarian, 453 and SKBR3, previously shown to be resistant to ACP, were also resistant to up to 20 ng/ml VT1.

The 1, 2, 3 and 4 cells were from ovarian cancer patients; the 453 cells were from a breast cancer patient; 231 and SKBR3 are breast adenocarcinoma cell lines, and 5, SKOV3 and SKOVLB are adenomacarcinous ovarian cancer cell lines. The lines 1, 453 and SKBR3, resistant to ACP, were co-resistant to VT1. FIG. 5 shows VT sensitive and resistant cell lines tested for the presence of $Gb_3$ by VT binding in tlc overlay. Glycolipid from an equal number of cells were extracted and separated by tlc prior to toxin binding. In FIG. 5, lane 1:SKBR3, lane 2:468, lane 3:231, lane 4:453, lane 5 $Gb_3$ standard, lane 6:SKOV3, lane 7:SKOVLB. Cell lines SKBR3, 468, 231 and 453 are derived from breast tumours. Only 231 is sensitive to VT1. SKOVLB is a multiple drug resistant ovarian tumour cell line derived from SKOV3.

Figure 3:
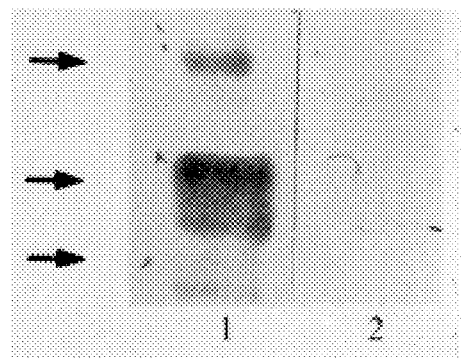
FIG. 3 represents VT1 contained within ACP preparation binding to $Gb_3$ (and $Gb_2$).
Figure 4:
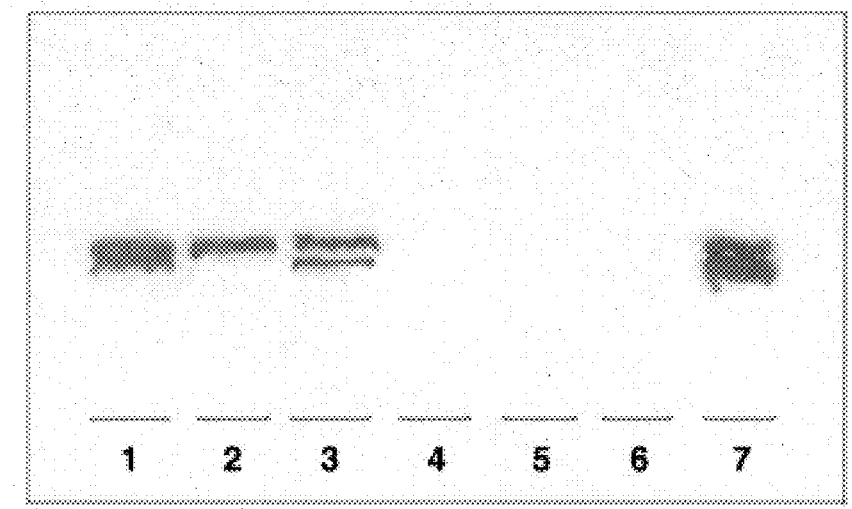
FIG. 4 represents VT thin layer chromatography overlay of ovarian tumour and ovary glycolipids.

Ovarian tumour cells were highly sensitive to VT (FIG. 3) and contained elevated levels of the VT receptor, $Gb_3$ (FIG. 4). Breast cancer cells were for the most part, toxin resistant (FIG. 3) and receptor negative (FIG. 5). Low levels of $Gb_3$ were detected in normal ovarian tissue but these were markedly elevated for the ovarian tumour tissue samples.

The specific elevation of $Gb_3$ in ovarian tumours as opposed to normal ovary tissue provides the feasibility of using the toxin in the management of this malignancy. Ovarian tumours are often refractory to chemotherapy and prognosis is poor. Indeed, preliminary phase 1 clinical trials using a ACP injected directly into skin malignancies (Mycosis fungoides) have proven successful without adverse systemic effects.

Figure 6A:
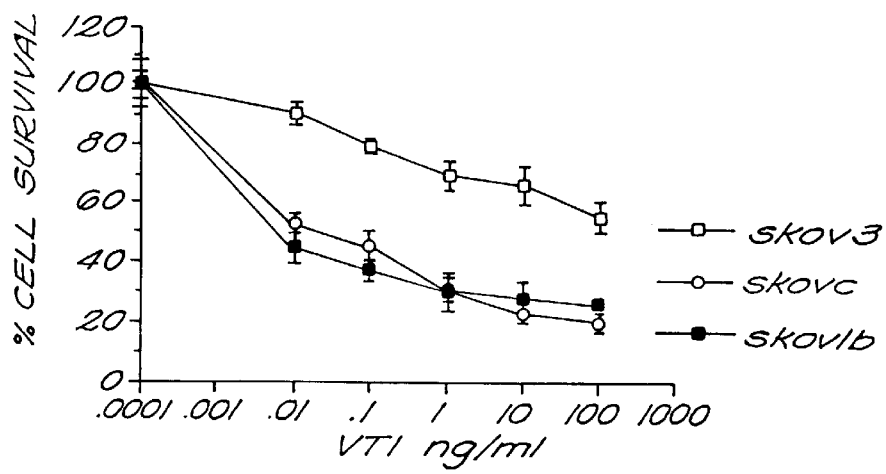
FIGS. 6A–6C represents in three graphs ovarian cell line sensitivity to VT1 (FIG. 6A), VT2 (FIG. 6B) and VT2c (FIG. 6C)
Figure 6B:
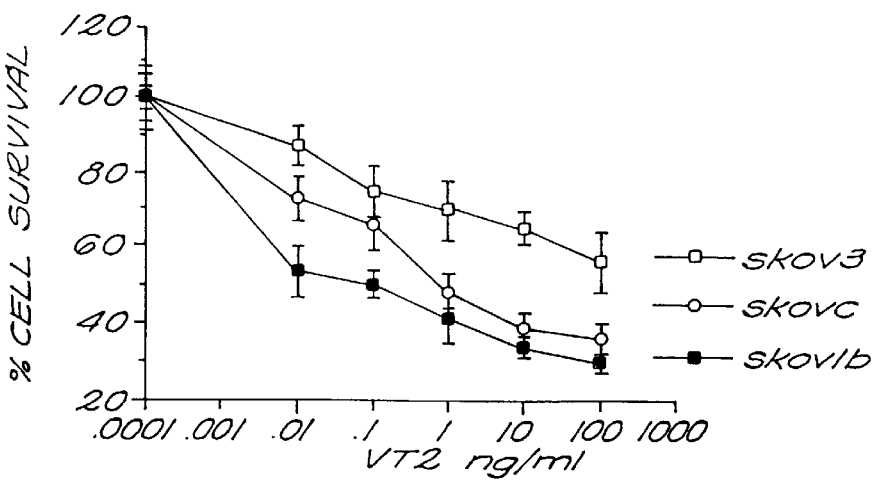
Figure 6C:
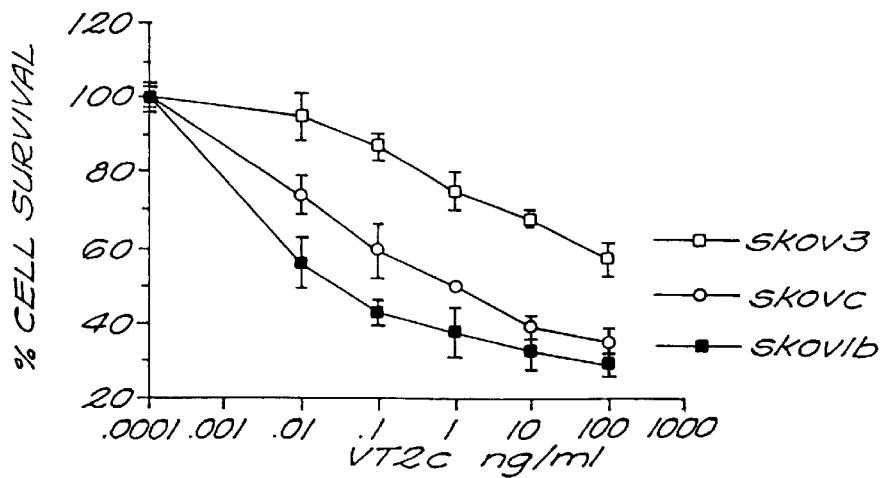

With reference now to FIG. 6, human derived ovarian tumour cell lines were tested for VT1 (FIG. 6A), VT2 (FIG. 6B), and VT2c (FIG. 6C) sensitivity. The cells were grown to confluence in 48-well plates, then incubated for 48 hrs. in the presence of increasing doses of VTs. SKOVLB, the multiple drug resistant variant of SKOV3 ovarian line, showed the most sensitivity to VT's with SKOVLC being the next most sensitive to the VTs.

We have found that both drug resistant cells are approximately 500 to 1000 times more sensitive to verotoxin cytotoxicity than the parental SKOV3 cell line.

Figure 7:
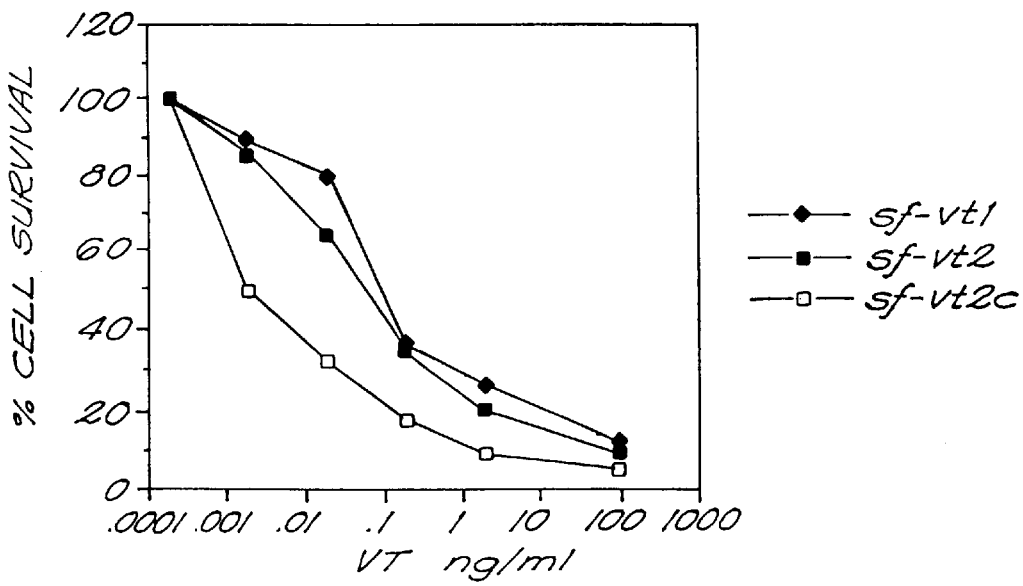
FIG. 7 represents glioblastoma multiforme cell line sensitivity to VT1. VT2 and VT2c.

FIG. 7 shows the effect after 48 hrs. of treatment of the brain tumour SF-539 cell line derived from a recurrent, right temporoparictal glioblastoma multiform with VT1, VT2, and VT2c. This cell line, as others, was highly sensitive to VTs.

Figure 8:
FIG. 8 represents the distribution of labelled VT1 B subunit (VTB-$^{131}$I) administered IP (inter-peridinually) in a $Gb_3$ tumour bearing nude mouse.

FIG. 8 provides the results from imaging a nude mouse with $^{131}$I-VT1B (CPM distribution in different organs). VT1B-$^{131}$I cpm distribution in nude mouse with implanted ovarian tumour showed that a considerable amount of radiolabled VT1B had been concentrated in the ovarian tumour. Only a trace amount of VT1B was located in the brain where the potential VT1 side effect was considered. Since the lung in human adult is not the site of concern for VT1 toxicity this does not present a problem for treatment of human adult with ovarian tumour. In addition the CPM in kidney includes the excreted radiolabelled VT1 B subunit. Accordingly, based on this test, imaging with labelled VT1 B subunit can be a very useful method for screening the susceptible patient to VT1 cytotoxicity.

Figure 9:
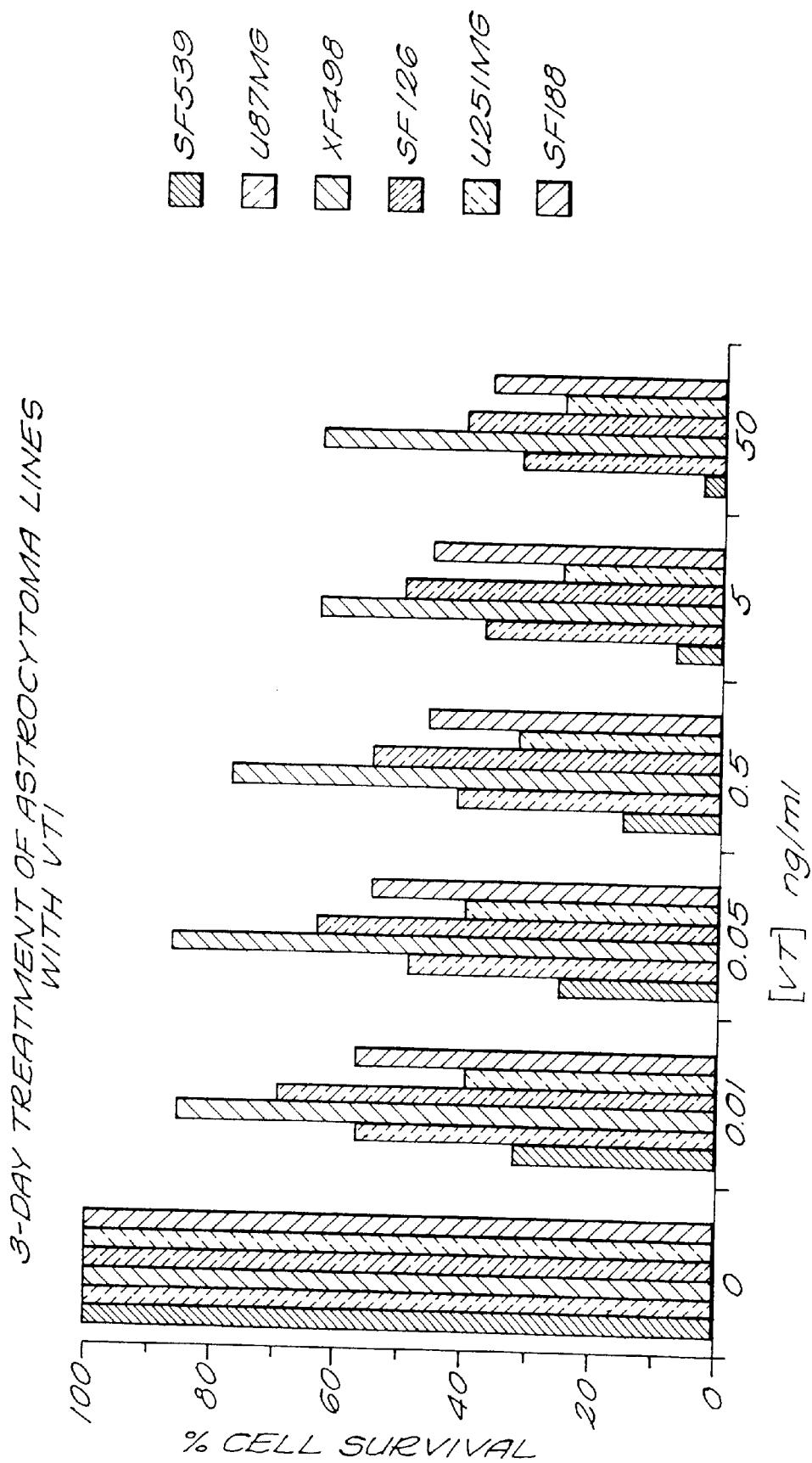
FIG. 9 represents the results of a three-day treatment of several human astrocytoma cell lines with VT1.

FIG. 9 shows the sensitivity of a variety of human astrocytoma cell lines to VT1. All these cells contain $Gb_3$ but show variable sensitivity to VT1 induced cytotoxicity. This suggests that certain astrocytomas will be more susceptible to verotoxin than other astrocytomas. This is important since astrocytomas are very refractory to treatment at the present time and cell sensitivity in vitro to concentrations as low as 5 ng per/ml is rare.

Figure 10A:
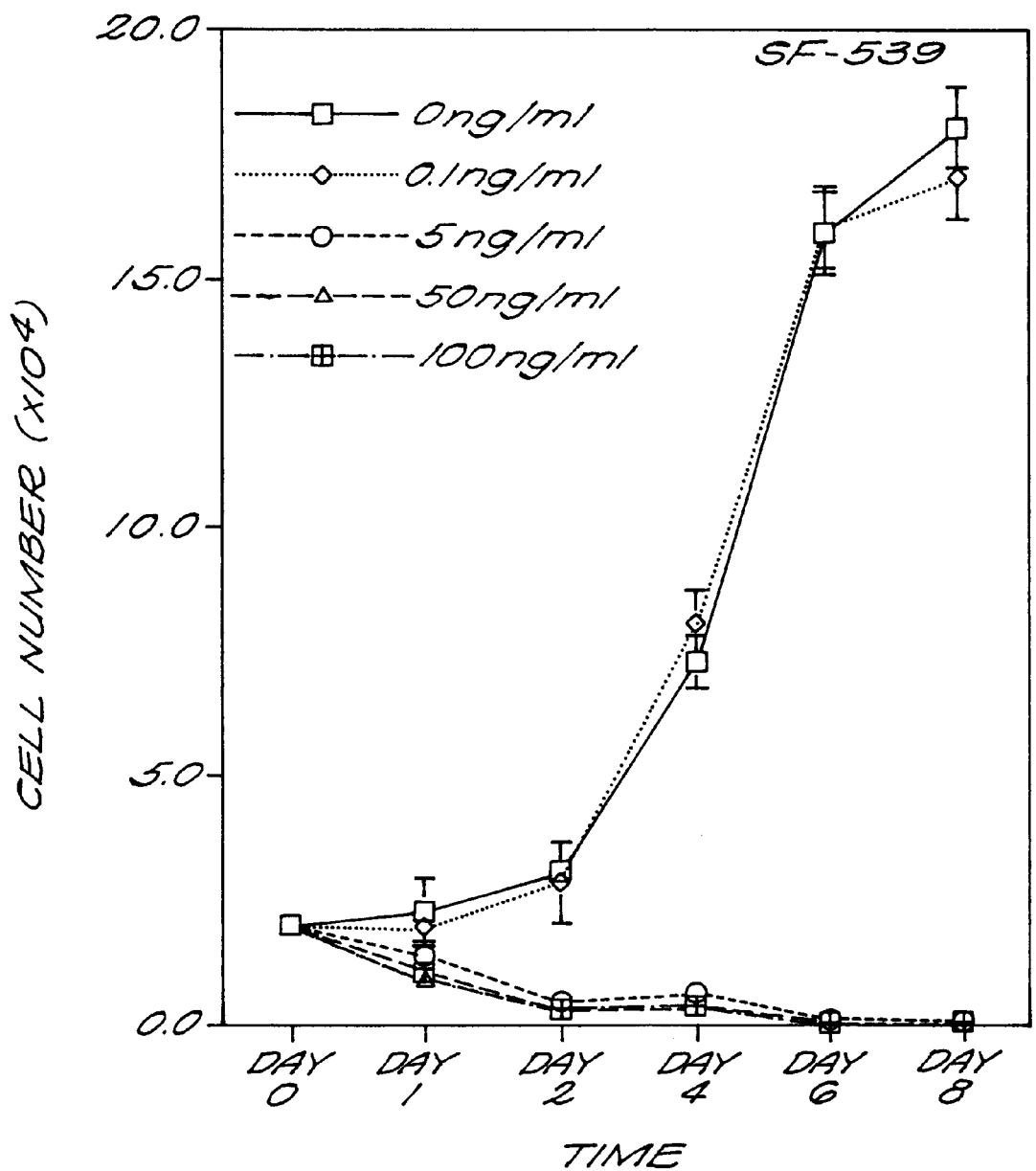
FIGS. 10A–10G represents a graph of the anti-proliferative effects of VT1 on human astrocytoma cells.
Figure 10C:
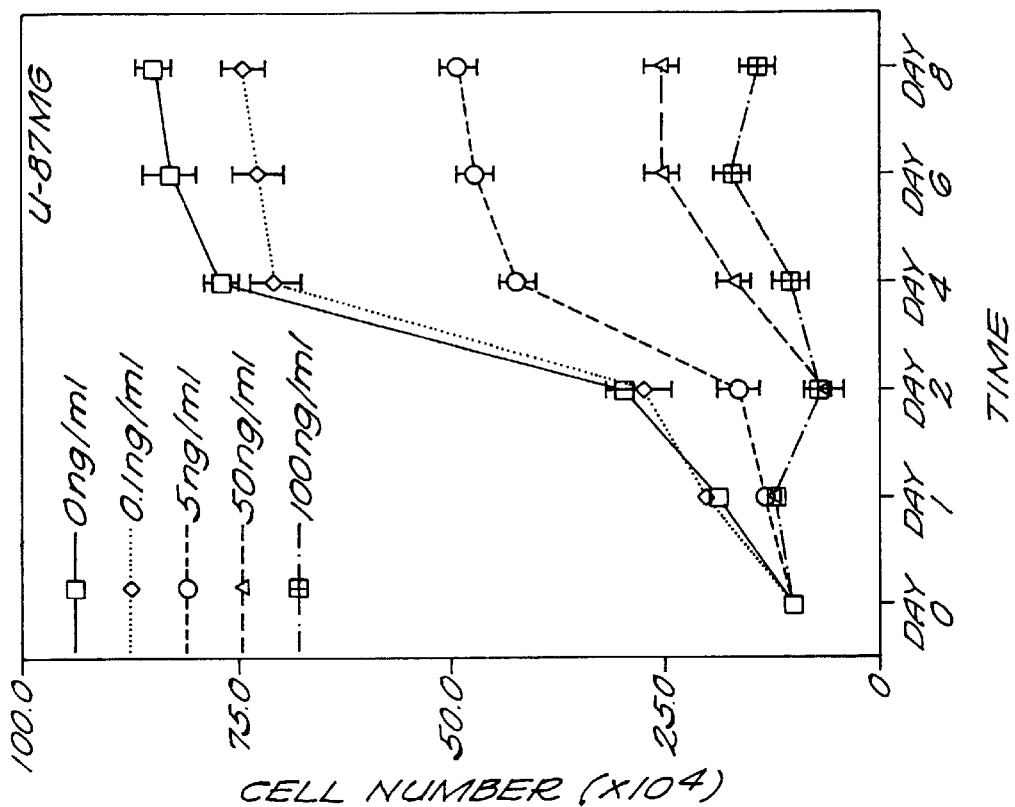
Figure 10B:
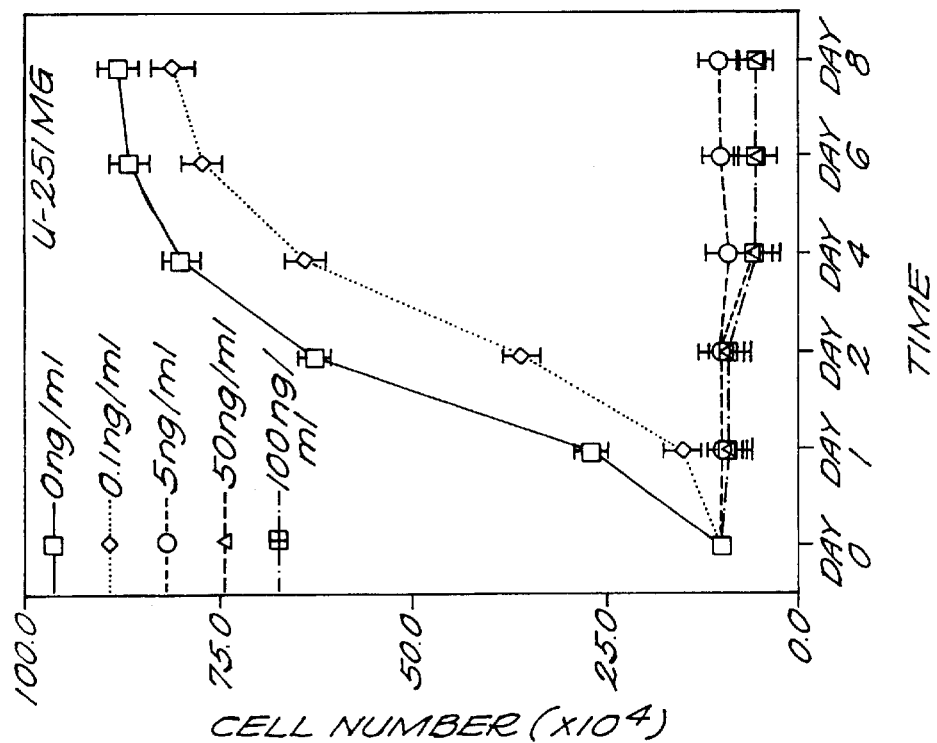
Figure 10E:
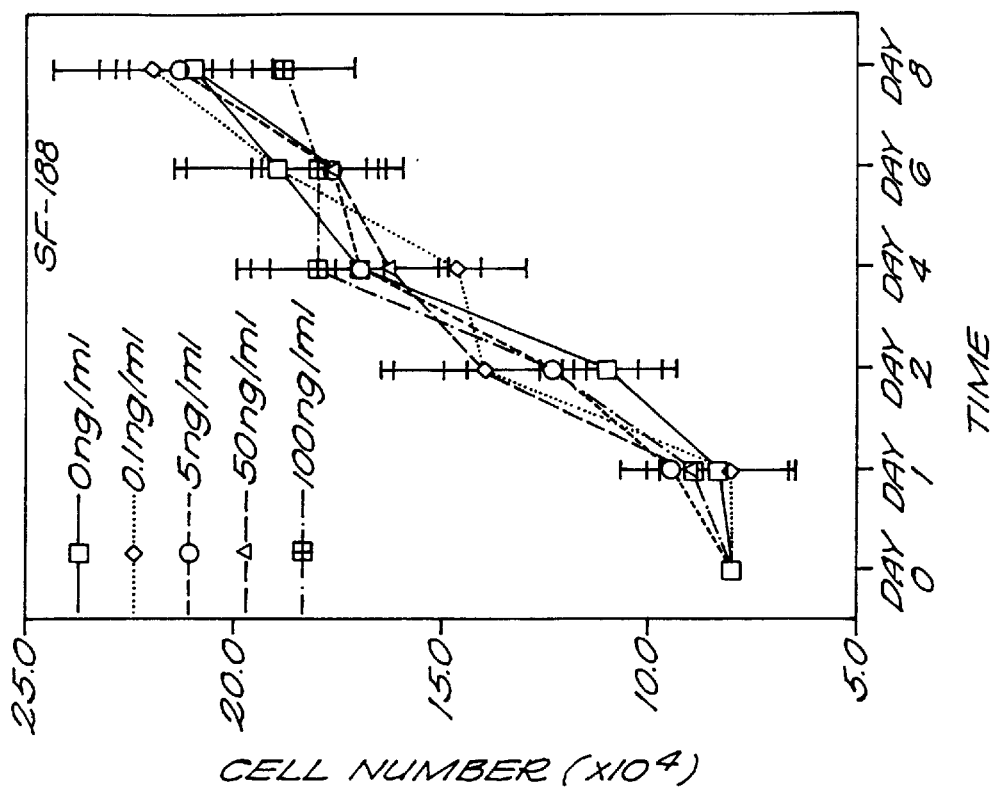
Figure 10D:
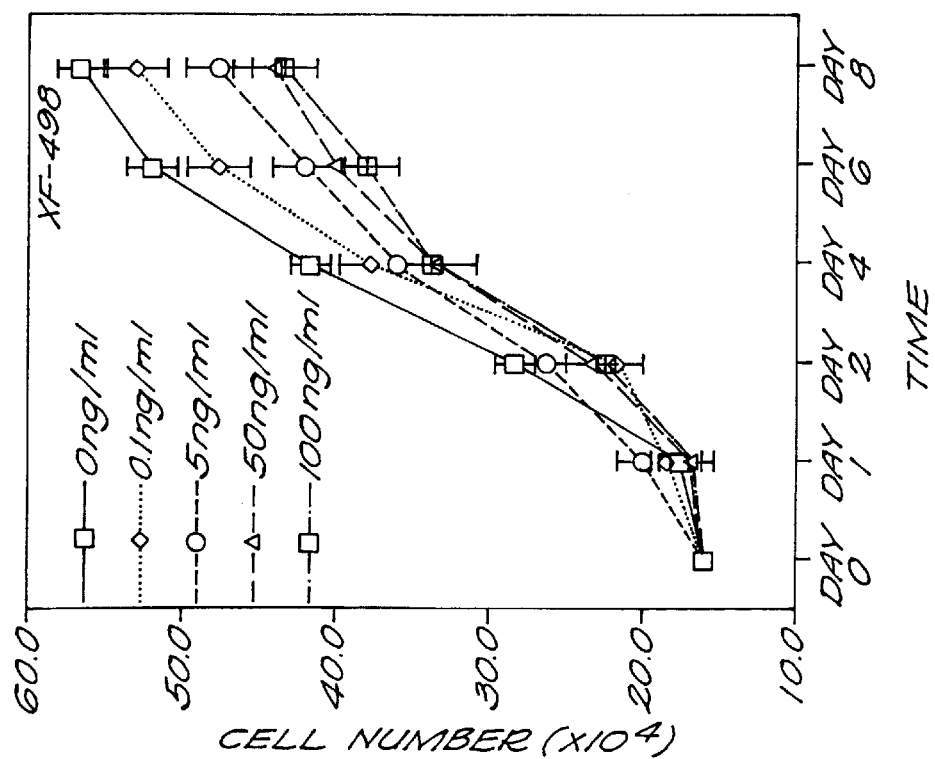
Figure 10G:
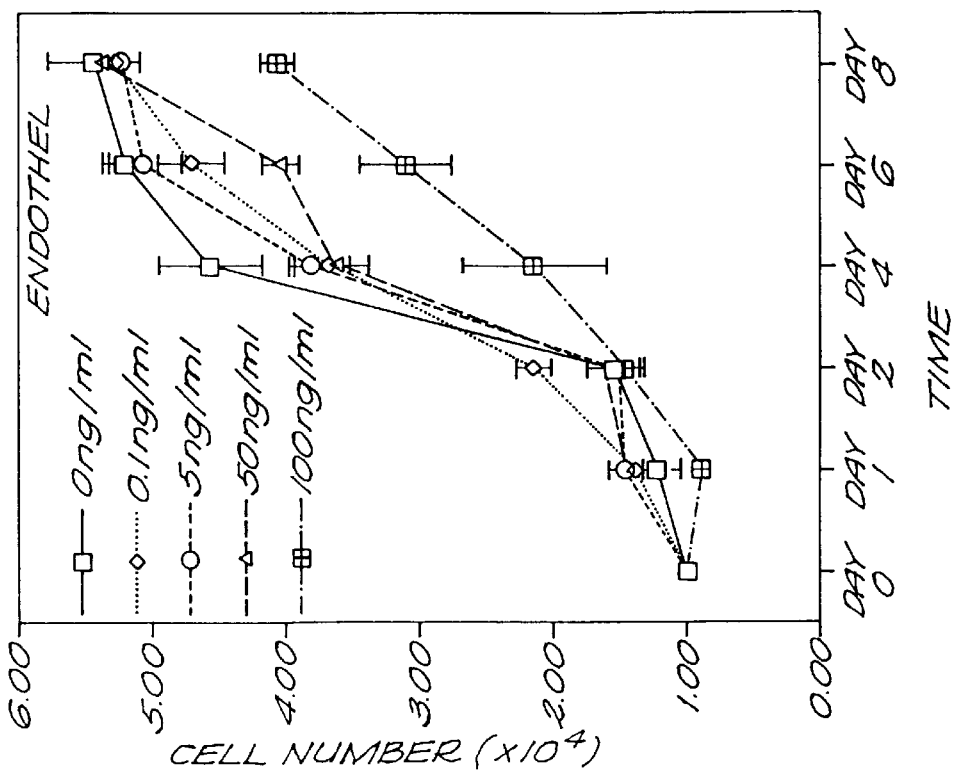
Figure 10F:
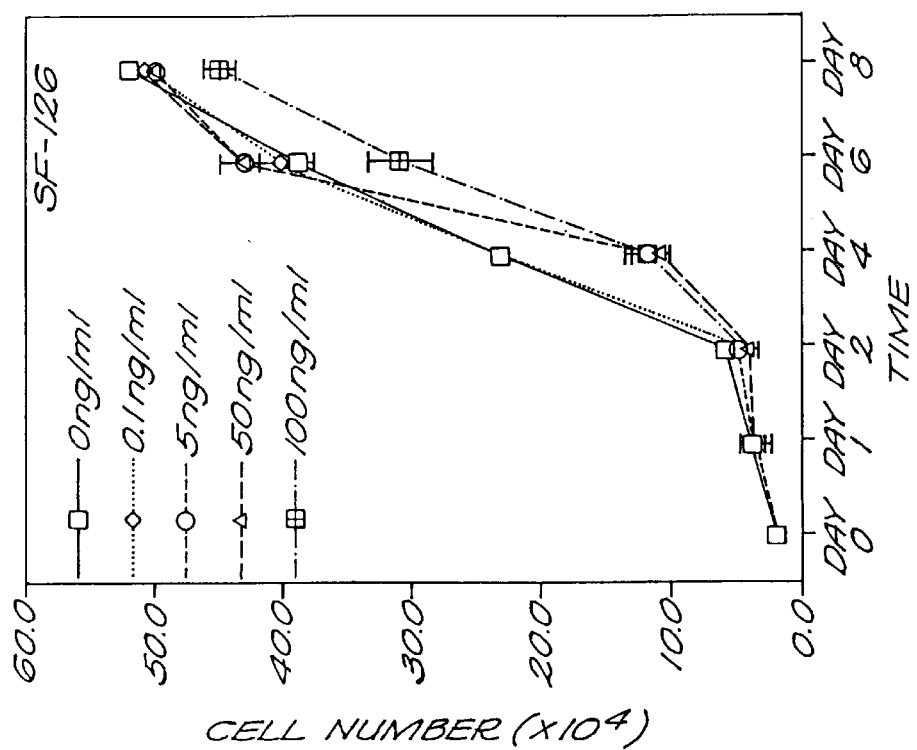

FIGS. 10A–10G show the anti-proliferative effects of VT1 on human astrocytoma cells. All astrocytoma cell lines showed at least some inhibition of growth following VT1 treatment. The most sensitive cell line was SF-539 (FIG. 10A), and the least sensitive was SF-126 (FIG. 10F). Human cerebral capillary endothelial cells were largely resistant to the growth-inhibitory effects of VT1 except at high doses (100 ng/ml) (FIGS. 10G). U-251 MG and U-87 MG were sensitive to VT1 (FIGS. 10B and 10C), whereas XF 498 and SF-188 were somewhat less sensitive to VT1 (FIGS. 10D, 10E and 1E) than were U-251 MG and U-87 MG.

Figure 11A:
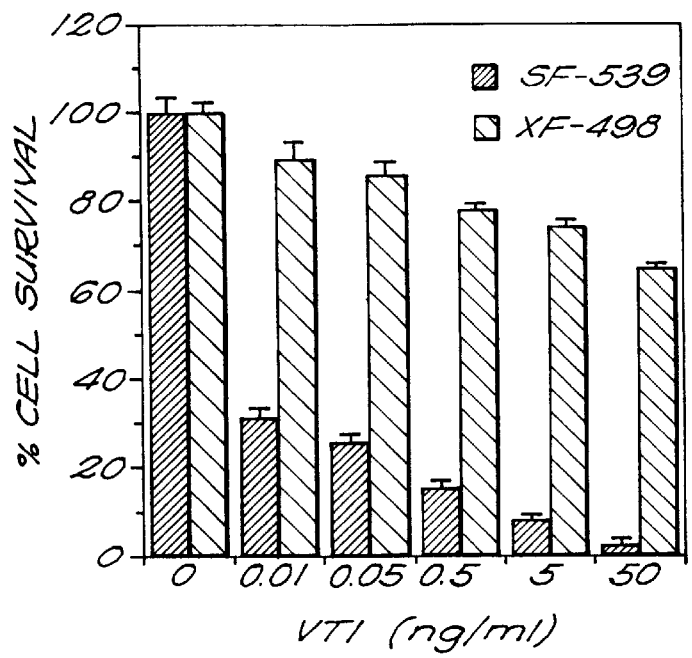
FIGS. 11A and 11B provide a comparison of SF-539 and XF-498 sensitivity to VT1 holotoxin.
Figure 11B:
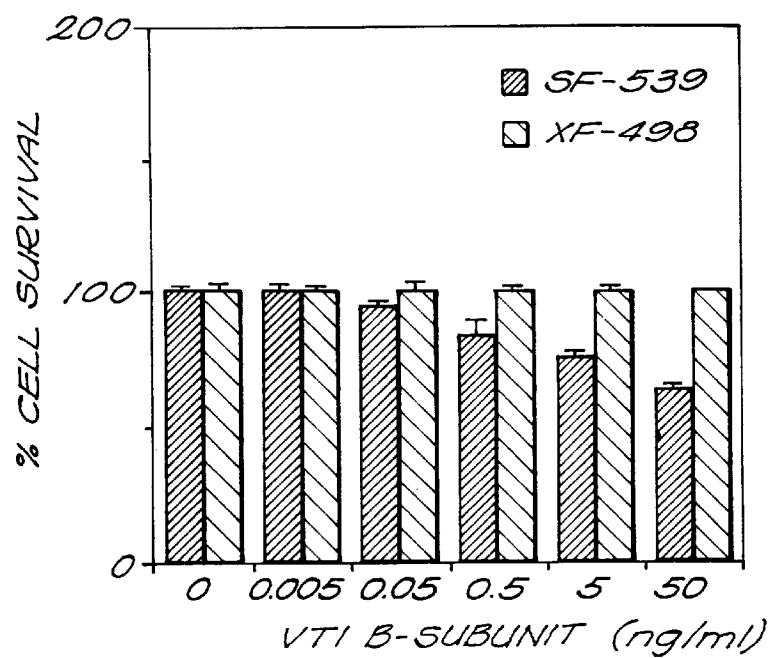

FIGS. 11A and 11B provide a comparison of SF-539 and XF-498 sensitivity to VT1 holotoxin (upper panel) and B-subunit (lower panel). Forty-eight hrs following the treatment of SF-539 and XF-498 cells in monolayer culture, the percent cell survival was calculated. VT1 was cytotoxic to SF-539 astrocytoma cells at doses as low as 0.01 ng/ml (upper panel). XF-498 cells were resistant to VT1 holotoxin. When the VT1 B-subunit was employed, only SF-539 was sensitive to this toxin (lower panel).

Figure 12A:
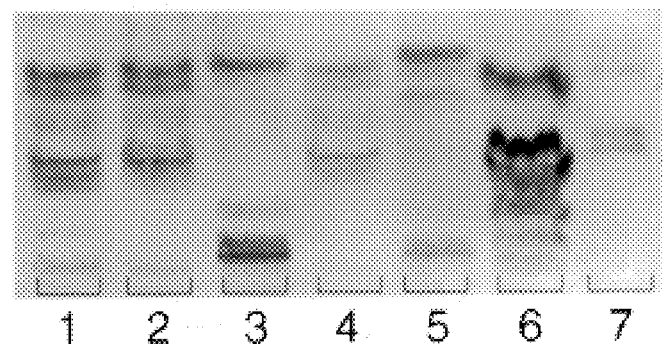
FIGS. 12A and 12B represent the detection of the VT-Receptor glycolipid, $Gb_3$ in human astrocytoma cell lines.
Figure 12B:
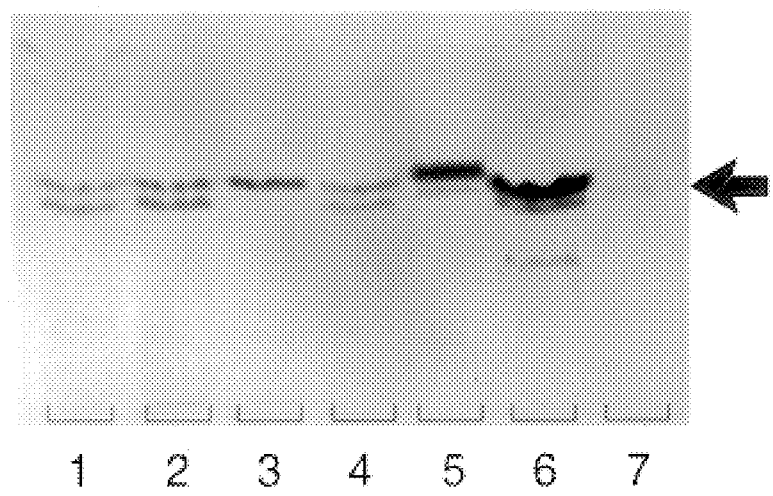

FIGS. 12A and 12B represent the detection of the VT-Receptor glycolipid, $Gb_3$ in human astrocytoma cell lines. Astrocytoma neutral glycolipids were prepared from $1 \times 10^6$ cells and separated by TLC. (A) Glycolipids were visualized by orcinol and bands representing $Gb_3$ are seen in all astrocytoma cell lines. (B) The same blot was assayed by VT1 overlay. In this study, VT1 binds to $Gb_3$ extracted from astrocytoma cells as shown (arrow). SF-539 astrocytoma cells showed maximal binding of $Gb_3$/VT1. Lane 1, U87 MG; lane 2, U251 MG; lane 3, SF-126; lane 4, SF-188; lane 5, XF-498; lane 6, SF-539, lane 7, standard $Gb_3$ (0.3 ug/ml).

Figure 13:
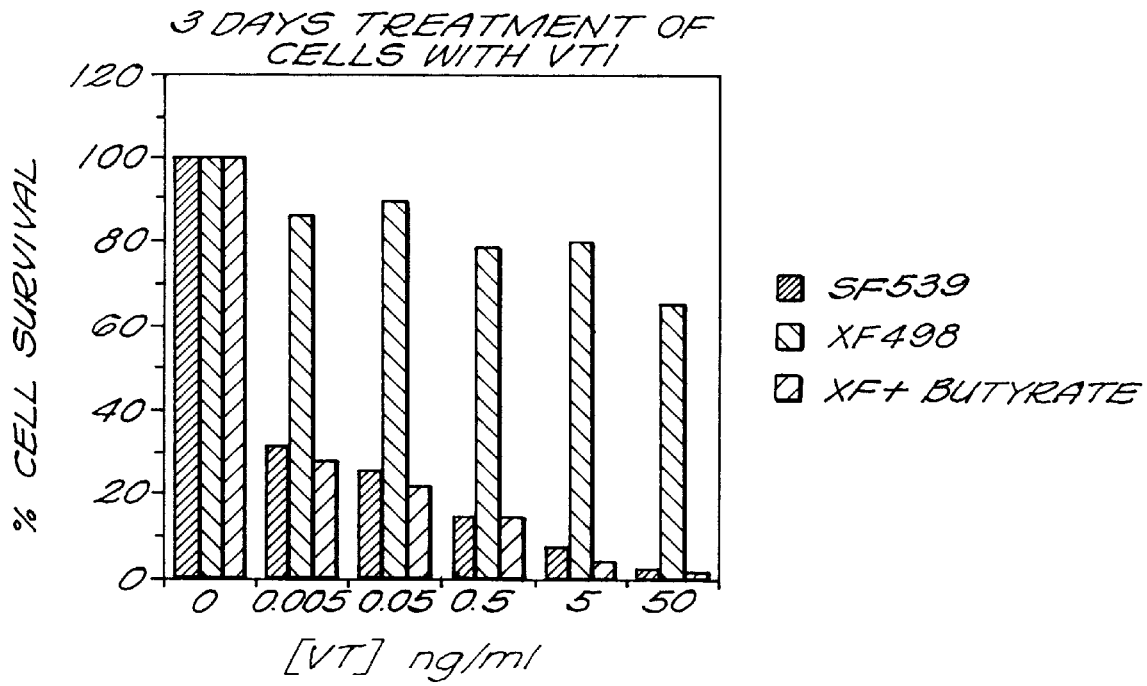
FIG. 13 shows the sensitivity of two astrocytoma cell lines to VT1 after sensitizing culture.
Figure 14:
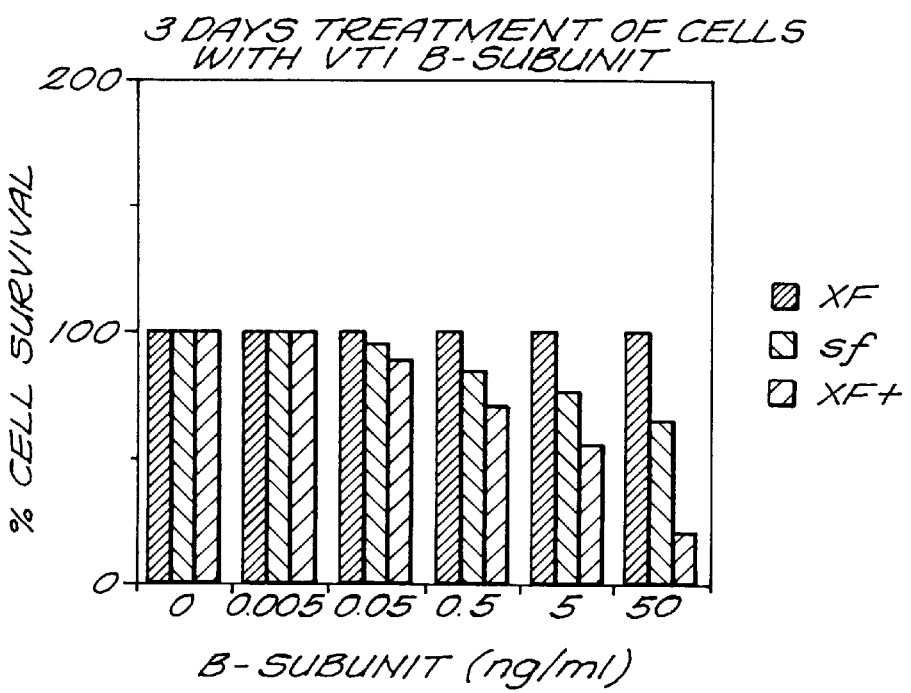
FIG. 14 shows the sensitivity to the B subunit of verotoxin VT1 of the two cell lines used in tests shown in FIG. 13.

FIG. 13 compares the sensitivity of two astrocytoma cell lines SF539 (sensitive), XF498 (less sensitive) and XF 498, following three days of culture of XF498 in sodium butyrate. It is seen that the sensitivity of XF498 is increased to that or even more than that of the most sensitive cell line SF539. FIG. 14 shows the same effect for the B subunit of verotoxin 1.

Anti-Proliferative Effects of Verotoxin on Human Astrocytoma Cells:

FIGS. 10A–10G show that all astrocytoma cell lines studied were sensitive to VT1. The most sensitive cell line in terms of growth inhibition was SF-539 (FIG. 10A) and the least sensitive was SF-188 (FIG. 10E). When treated with other members of the VT family including VT2, and VT2c, SF539 was growth inhibited. VT-1 was the most potent species (FIG. 11). Interestingly, human cerebral endothelial cells were largely resistant to the growth inhibitory and cytotoxic effects of VT-1 (FIG. 10G). Only when doses as high as 100 ng/ml were used were endothelial cells inhibited.

A comparison between the sensitivity of SF 539 and XF498 for VT1 and VT1 B subunit is shown in FIG. 11A and FIG. 11B. XF498 cells were considerably less sensitive to the B subunit than to the VT-1 holotoxin. By comparison, SF 539 astrocytoma cells were significantly more sensitive to the B subunit alone than were XF 498 astrocytoma cells, since 50% cell death was observed in the presence of 50 ng/ml.

VT-Receptor Analysis of Human Astrocytoma Cells:

The glycolipid profile of the 6 human astrocytoma cell lines analyzed for $Gb_3$ content as detected with orcinol is shown in FIG. 12A. All of the astrocytollia cell lines expressed significant levels of $Gb_3$ and showed binding with VT1 in the overlay assay used (FIG. 12B). SF-539 cells expressed the highest levels of $Gb_3$ with maximal binding to VT1.

Flow Cytometric Analysis:

To determine the extent of astrocytoma cells death by apoptosis, cells were analysed by flow cytometry. SF-539 and XF-498 astrocytoma cells exposed to VT1 (10 ng/ml) revealed the characteristic features of apoptosis. As a result of chromatin condensation and DNA cleavage, apoptotic cells show less propidium iodide fluorescence than viable cells and can be quantified as the "subdiploid" population or pre-G1 position in cell cycle (FIG. 13, arrow head). Presence of cells with fractional DNA content, typical of apoptosis was more marked in SF-539 than XF-498 cells. A cell cycle analysis of the non-apoptotic cell population revealed marked differences in the proportion of cells in the respective phases of the cell cycle. In VT1-sensitive SF-539 cells, a pronounced loss of S phase cells from 33 to 15 and 10% was seen, whereas with the less VT1 sensitive XF-498 cells, the loss of S phase cells observed was only 75 to 69 and 65%. Changes in the proportion of cells in G2-M phase were also seen (FIG. 13).

Propidium iodide stains:

For detection of apoptotic morphology in cells treated with VT1 or VT1 B-subunit, permeabilized SF-539 and XF-498 cells were stained with the DNA-intercalating agent propidium iodide and were analyzed by fluorescence microscopy. VT1 treated cells displayed characteristic features of apoptosis, such as marked reduction in diameter, condensed chromatin. Nuclear segmentation and subnuclear bodies were prominent in cells treated with VT1 B-subunit for 1.5 or 10 hours.

Ultrastructural Analysis of VT-Treated Astrocytoma Cells:

By electron microscopy, VT1-treated astrocytoma cells (SF-539, XF-498) demonstrated characteristic features of apoptosis such as, blebbing of the cytoplasmic membrane, fragmentation of heterochromatin, condensation of the nucleolar membrane, loss of cell junctions and microvilli, nuclear disintegration, and apoptotic bodies.

The results herein show that VT1 inhibits the growth of a series of human astrocytoma cell lines. All cell lines showed significant sensitivity to VT1, contained the $Gb_3$ receptor for VT, and demonstrated ultrastructural features indicative of apoptosis following VT treatment. These results show that VTs provide the basis of new agents active against human astrocytoma cells. The results show that the most toxin sensitive astrocytoma cell line, SF-539, is also highly sensitive to B subunit induced apoptosis.

Definitive morphological evidence of apoptosis (nuclear shrinkage and choromatine condensation) were observed within 1.5 hrs of toxin or B subunit administration to astrocytoma cells. This is considerably more rapid than has previously been described for induced apoptosis by anticancer drugs. Accumulation of VT1-treated astrocytoma cells in pre-G1 position in cell cycle (FIG. 13) is strong evidence for apoptosis. Additional evidence in support of VT1 causing apoptosis in sensitive astrocytoma cells include nuclear staining with propidium iodide and ultrastructural alterations indicative of apoptosis.

We have found that there was relative insensitivity of human cerebral capillary endothelial cells to VT.

While the invention has been described in detail and with reference to specific embodiments thereof, it will be apparent to one skilled in the art that various changes and modifications can be made therein without departing from the spirit and scope of the invention.

We claim:

1. A method of treating mammalian neoplasia comprising treating said mammal with a non-lethal, anti-neoplasia effective amount of a verotoxin, wherein said neoplasia is ovarian cancer.

2. A method of treating mammalian neoplasia comprising treating said mammal with a non-lethal, anti-neoplasia effective amount of a verotoxin, wherein said neoplasia is Mycosis fungoides.

3. A method of treating mammalian neoplasia comprising treating said mammal with a non-lethal, anti-neoplasia effective amount of a verotoxin, further comprising treating said mammal with a non-lethal effective, sensitizing amount of a sensitizer.

4. The method of claim 3, wherein said sensitizer is sodium butyrate.

5. The method of claim 3, comprising applying said sensitizer and said verotoxin to the locus of the neoplastic cells.

6. A method of treating mammalian neoplasia comprising treating said mammal with a non-lethal, anti-neoplasia effective amount of the pentameric B subunit of verotoxin, wherein said neoplasia is selected from brain, ovarian, breast and skin cancer.

7. The method of claim 6, wherein said brain cancer is an astrocytoma.

8. A method of treating mammalian neoplasia comprising treating said mammal with a non-lethal, anti-neoplasia effective amount of the pentameric B subunit of verotoxin, further comprising treating said mammal with a non-lethal effective, sensitizing amount of a sensitizer.

9. The method of claim 8, wherein said sensitizer is sodium butyrate.

10. The method of claim 8 comprising applying said pentameric B subunit and said sensitizer to the locus of the neoplastic cells.

11. A method of treating mammalian neoplasia comprising treating said mammal with a non-lethal, anti-neoplasia effective amount of a verotoxin, wherein said neoplasia is selected from the group consisting of brain, ovarian, breast and skin cancer.

12. The method of claim 11, wherein the brain cancer is an astrocytoma.

* * * * *